(12) United States Patent
Engel et al.

(10) Patent No.: US 9,309,567 B2
(45) Date of Patent: Apr. 12, 2016

(54) METHOD FOR POLYMERASE CHAIN REACTIONS WITH USE OF A DNA POLYMERASE WITH PROOFREADING PROPERTIES

(75) Inventors: Holger Engel, Hilden (DE); Ralf Peist, Düsseldorf (DE)

(73) Assignee: QIAGEN GmbH, Hilden (DE)

(*) Notice: Subject to any disclaimer, the term of this patent is extended or adjusted under 35 U.S.C. 154(b) by 1252 days.

(21) Appl. No.: 11/540,492

(22) Filed: Sep. 28, 2006

(65) Prior Publication Data
US 2007/0082355 A1 Apr. 12, 2007

(30) Foreign Application Priority Data
Oct. 5, 2005 (DE) .......................... 10 2005 047 617

(51) Int. Cl.
*C12Q 1/68* (2006.01)
(52) U.S. Cl.
CPC .......... *C12Q 1/686* (2013.01); *C12Q 2525/113* (2013.01); *C12Q 2525/125* (2013.01); *C12Q 2525/179* (2013.01); *C12Q 2525/186* (2013.01)
(58) Field of Classification Search
None
See application file for complete search history.

(56) References Cited

U.S. PATENT DOCUMENTS

| | | | | |
|---|---|---|---|---|
| 5,627,054 A * | 5/1997 | Gillespie | ...................... | 435/91.2 |
| 5,677,152 A | 10/1997 | Birch et al. | ................... | 435/91.2 |
| 5,736,333 A * | 4/1998 | Livak et al. | ................... | 435/6.12 |
| 5,830,712 A * | 11/1998 | Rampersad et al. | ......... | 435/91.1 |
| 5,843,669 A * | 12/1998 | Kaiser et al. | ...................... | 435/6 |
| 6,300,069 B1* | 10/2001 | Missel et al. | ...................... | 435/6 |
| 6,830,902 B1* | 12/2004 | Astatke et al. | ............... | 435/91.1 |

FOREIGN PATENT DOCUMENTS

| | | | | | |
|---|---|---|---|---|---|
| AU | WO 2004003228 A1 * | 1/2004 | | ........... | C12Q 1/6858 |
| EP | 0 771 870 B1 | 2/1999 | | | |
| EP | 0 962 526 B1 | 11/2005 | | | |
| GB | 2293238 A * | 3/1996 | | | |
| WO | WO 9728279 A2 * | 8/1997 | | | |

OTHER PUBLICATIONS

Dean et al. Rapid amplification of plasmid and phage DNA using phi29 DNA polymerase and multiply-primed rolling circle amplification. Genome Research (2001) 11: 1095-1099.*
The 2005-2006 New England Biolabs catalog (published 2004), p. 91.*
Yang et al. High fidelity PCR with an on/off switch mediated by proofreading polymerases combining with phosphorothioate-modified primer. Biochemical and Biophysical Research Communications (2005) 328(1): 265-272.*
Nagai et al. Genetic heterogeneity of the epidermal growth factor receptor in non-small cell lung cancer cell lines revealed by a rapid and sensitive detection system, the peptide nucleic acid-locked nucleic acid PCR clamp. Cancer Research (2005) 65(16): 7276-7282.*
Fujii et al. A new DNA typing method of D1S80 marker by capillary electrophoresis of ABI 310 Genetic Analyzer. Japanese Journal of Forensic Science and Technology (2006) 11(1): 41-52.*
Bustin, S.A. Absolute quantification of mRNA using real-time reverse transcription polymerase chain reaction assays. Journal of Molecular Endocrinology (2000) 25: 169-193.*
Shen et al. Triplex-forming oligodeoxynucleotides targeting survivin inhibit proliferation and induce apoptosis of human lung carcinoma cells. Cancer Gene Therapy (2003) 10: 403-410.*
Nnis, M.A. PCR Protocols: A Guide to Methods and Applications (1990) pp. 3-12.*
Dietrich et al. FEMS Microbiology Letters (2002) 217: 89-94.*
De Noronha, Carlos M.C., and Mullins, James I., "Amplimers with 3'-Terminal Phosphorothioate Linkages Resist Degradation by Vent Polymerase and Reduce Taq Polynierase Mispriming,"*PCR Methods and Applications*, 2(1): 131-136 (1992).
Skerra, Arne, "Phosphorothioate Primers Improve the Amplification of DNA Sequences by DNA Polymerases with Proofreading Activity," *Nucleic Acids Research*, 20(14), 3551-3554 (1992).
"SuperScript™ One-Step RT-PCR with Platinum® *Taq*," www.invitrogen.com, downloaded Mar. 16, 2008, published 2003.
"Titanium™ One-Step RT-PCR Kit User Manual," www.clontech.com, downloaded Mar. 16, 2008, published Aug. 31, 2007.
"Throw Away the Script! Using ImProm-II™ Reverse Transcription System for Coupled RT-PCR," www.promega.com, downloaded Mar. 16, 2008, published 2001.
"TaqMan® One-Step RT-PCR Master Mix Reagents Kit Protocol," www.appliedbiosysterns.com, downloaded Mar. 16, 2008, published Nov. 2006.

* cited by examiner

*Primary Examiner* — Angela M Bertagna
(74) *Attorney, Agent, or Firm* — Seed IP Law Group PLLC

(57) ABSTRACT

The present invention concerns a method for a polymerase chain reaction, in which a template nucleic acid, at least one primer, deoxyribonucleoside triphosphates as well as a DNA polymerase with proofreading activity are used. In addition, according to this invention, at least one target substrate is added to the polymerase chain reaction, whereby the efficiency of the DNA polymerase with proofreading activity is significantly increased. Any molecule that reduces or, in the optimal case, blocks the 3',5'-exonuclease activity of the DNA polymerase used is suitable as target substrate. Technical solutions for the added substrate (target substrate) are in particular single stranded, linear oligonucleotides, hairpin oligonucleotides and RNA and DNA molecules. Furthermore, a kit is disclosed which comprise the required reagents for the implementation of the method according to the invention.

12 Claims, 22 Drawing Sheets

METHOD FOR POLYMERASE CHAIN REACTIONS WITH USE OF A DNA POLYMERASE WITH PROOFREADING PROPERTIES

This application claims the benefit of German Patent Application No. 10 2005 047 617.1, filed Oct. 5, 2005, which is incorporated by reference in its entirety.

The present invention concerns a method for the polymerase chain reaction, in which a DNA polymerase that exhibits proofreading properties is used.

The polymerase chain reaction method ("PCR") is a method employed in gene technology which succeeds in propagating a few molecules of any DNA sequence in vitro in a short time by factors of $10^6$ to $10^8$. Typically required are two synthetically prepared oligodeoxynucleotide primers, approximately 15 to 30 nucleotides long whose sequences are complementary to the start and end sequences of the sister strand of the DNA to be propagated ("amplified"), a mixture of 4'-deoxynucleotide-5'-triphosphates as well as a thermostable DNA polymerase that can tolerate at least a short time of heating to 95° C. without loss of function.

Often thermostable DNA polymerases that show a "proofreading" property (so-called "high fidelity DNA polymerases") are also used in PCR. These high fidelity DNA polymerases are characterised by a low error rate and high accuracy in DNA synthesis. With the use of such high fidelity DNA polymerases, however, problems often arise to the effect that only a very small yield of PCR product is achieved, to the point of total failure of the PCR (that is, no PCR product is produced whatsoever). This problem occurs in particular when only a small amount of template nucleic acid or low primer concentration is available. The reason is likely to be the degradation of the template nucleic acid and the primer through the proofreading activity of the high fidelity DNA polymerase. This loss of template nucleic acid and primer then leads to a dramatic reduction in the rate of amplification, which in turn causes a reduced yield of PCR product or even the total failure of the PCR.

It has been demonstrated that those PCR primers that exhibit a phosphoro-phosphothioate linkage at their 3'-terminus in the DNA backbone are protected against degradation through the 3'-5'-exonuclease activity of the inserted high fidelity DNA polymerase. By the use of such primers, the yield and reliability of high fidelity PCR can be improved. See, for example, de Noronha, C. M. and Mullins, J. I., *Amplimers with 3'-terminal phosphoroPhosphothioat linkages resist degradation by vent polymerase and reduce Taq polymerase mispriming*, PCR Methods Appl, 1992. 2(2), 131-136; and Skerra, A., *PhosphoroPhosphothioat primers improve the amplification of DNA sequences by DNA polymerases with proofreading activity*, Nucleic Acids Res, 1992, 20(14), 3551-3554. The effect of such primers on the sensitivity and yield of high fidelity PCR was tested in line with the experiment for this invention. It became clear that the use of such primers exhibit a much smaller effect on sensitivity and yield of the high fidelity PCR than the underlying principle of the present invention.

The above-described observation now says that high fidelity DNA polymerases give rise to difficulties in reproducibility and sensitivity of the PCR reactions, especially when small quantities of templates are used. In many cases of suboptimal conditions, the PCR cannot be carried out successfully. A high fidelity PCR requires, therefore, much improvement, since it depends to a much greater extent on the amount of start template used than, for example, PCR with Taq polymerase.

In view of the above-described problems of the state of the art, it is therefore the task of the present invention to provide a polymerase chain reaction in which a high fidelity DNA polymerase can be used with low template nucleic acid starting material, and can still achieve a satisfactory yield of PCR product.

The invention solves this task through the method stated in independent claim 1 as well as through the kit stated in claim 67. Further advantageous aspects, embodiments and details of the invention arise from the dependent claims, the descriptions, the examples and the drawing.

Consequently, the present invention discloses a polymerase chain reaction, wherein a template nucleic acid, at least one primer, deoxyribonucleoside triphosphates and a polymerase with proofreading activity are used, whereby the reaction is characterised in that in the polymerase chain reaction at least one target substrate is added. Any molecule that reduces or, in the optimal case, blocks the 3'-5'-exonuclease activity of the DNA polymerase is suitable as target substrate. It could also be said, that the 3'-5'-exonuclease activity of the DNA polymerase used is deflected or diverted towards the target substrate.

The PCR product yield as well as the sensitivity and the reliability of the PCR with the use of high fidelity DNA polymerase is thus achieved, according to the invention, by a targeted deflection of surplus (unemployed) high fidelity molecules towards one of the target substrates added to the reaction (also called "feed"). The terms "target substrate" and "feed" are used synonymously within the context of the present invention. By this deflection towards an added substrate, the degradation of the primer and/or the template DNA by the proofreading activity of the high fidelity DNA polymerase is reduced in such a way, that a reliable implementation of the PCR reaction is possible under the conditions that, without addition of the "feed", only a small PCR product yield would be delivered, or even the total failure of the PCR. Thereby it is especially beneficial that a successful PCR is possible by use of the "feed" with clearly variable amounts of start template nucleic acids. In this way costly optimisation of the experimental conditions are significantly reduced, which also considerably decreases expenditure in time and material.

The added target substrate is characterised in that it has the ability to form double stranded structures under PCR conditions, which can serve as binding sites for the high fidelity DNA polymerase. The target substrate added should not disrupt the PCR reaction and, in addition, ideally be constructed, so that it does not participate in the PCR reaction at all (that is, is not amplified). There is then no disturbance in the amplification if, for example, no commonly occurring by-products are formed in disrupting quantities, or the feed DNA is detectable per se. A disruptive quantity is generally reached when the by-products generated are detectable as background in the PCR product analytical methods use, or they show a disruptive impact on subsequent applications, e.g. cloning, in vitro transcription/translation or mutagenesis.

Technical solutions for the added substrate (target substrate) are in particular single stranded, linear oligonucleotides, hairpin oligonucleotides and RNA and DNA molecules. Examples for possible formulations are specified in the following.

During use of the ProofStart DNA polymerase (QIAGEN GmbH, Hilden, Germany), it became clear that the use of a concentration of 1 µM for each of the two necessary primers makes the high fidelity PCR with ProofStart DNA polymerase (QIAGEN GmbH, Hilden, Germany) more stable. This is a higher concentration than that recommended for a standard PCR with Taq polymerase (typically 0.2-0.4 µM).

Not wanting to be fixed to this theory, the inventors of the present invention assume that the superior robustness of primers at a concentration of 1 µM could be due to the degradation of part of the primer by the ProofStart DNA polymerase.

The method according to the invention is feasible with all commercially available high fidelity DNA polymerases. These enzymes can either be used with or without "Hot Start" function. "Hot Start" can be carried out using all usual commercial methods including the blocking of enzyme activity with antibodies, or by chemical modification (compare for example U.S. Pat. No. 5,677,152, EP-A-0 771 870 and EP-A-0 962 526).

According to the invention a kit is also provided. Such a kit comprises at least one container with a target substrate or "feed" within the meaning of this invention. In a preferred embodiment this kit also comprises a high fidelity DNA polymerase (DNA polymerase with proofreading activity) in a preferred mould, one or more PCR buffers, dNTPs, a solution with $Mg^{2+}$ ions and/or one or more suitable PCR additives, such as betaine, polyethylene glycol (PEG), dextran, glycerol, dimethylsulfoxide (DMSO), bovine serum albumin (BSA), single stranded DNA-binding protein, (non-ionic) surfactants or other suitable substances. Each component can be alone or formulated as a mixture of two or more components. Preferably, the kit according to the invention is designed to carry out the method according to the invention. Therefore, everything said concerning the method applies likewise to the kit.

The deflection of the high fidelity DNA polymerase is feasible using many different technical solutions, which are described in detail subsequently and whose functions are proved with data in the examples. The individual aspects of several embodiments are arbitrarily interchangeable, in so far as this is technically and reasonably feasible.

A first preferred embodiment of the invention concerns the addition of single stranded oligonucleotides as target substrates or "feed" to a PCR.

The applicable single stranded oligonucleotides of the invention are characterised in that they have the ability to form double strands under PCR conditions which can serve as binding sites for the high fidelity DNA polymerase. The added "feed" oligonucleotides should preferably also be so constructed, that they do not participate in the PCR reaction in an undesirable manner. Possible technical solutions as well as fundamental properties of the added "feed" oligonucleotides are described more closely in the following.

Prevention of the 3'-elongation of the target substrate or "feed" oligonucleotide by the DNA polymerase used can be desireable. In the preferred embodiment the "feed" oligonucleotide should not be elongated by the DNA polymerase, that is, not to serve as a primer itself. This can be achieved through modification of the 3'-terminus of the oligonucleotide, so that it can no longer be elongated by the high fidelity DNA polymerase. Several solutions are possible for this purpose, which could already be incorporated during the synthesis of the target substrate. These solutions include the attachment of dideoxynucleotides, inverse bases, RNA, abasic sites, spacers, dyes, quencher residues, e.g. Black Hole Quencher, Dabcyl, minor groove binders, modified bases, e.g. super bases or halogenated bases or base analogues, as well as all other plausible modifications to the sugar backbone and to the bases, and additional side groups that inhibit the ability of the high fidelity DNA polymerase to catalyse DNA synthesis. The preferred solution for the protection against extension of the primer is the integration of a 3'-phosphate group instead of the necessary 3'-OH group in a DNA oligonucleotide.

A further possibility concerns the prevention of the 3'-shortening of the target substrate by modification of the DNA backbone. In consequence of its 3'-5'-exonuclease activity, the high fidelity DNA polymerase is able to shorten a primer at the 3'-terminus, whereby a modification for prevention of 3'-elongation could undesirably be removed. This 3'-5'-exonucleic shortening can be prevented by a change or several changes in the backbone of the DNA. For this the preferred solution is the attachment of at least one phosphothioate instead of a phosphate in the sugar-phosphate backbone of the DNA oligonucleotide. In order to prevent 3'-5'-exonucleic shortening completely, it is sufficient to replace the phosphate in the backbone between the last and penultimate 3'-base of the DNA oligonucleotide with a phosphothioate. An appropriate substitution is shown in the following structural formula (structure of a DNA with phosphothioate modification in the backbone).

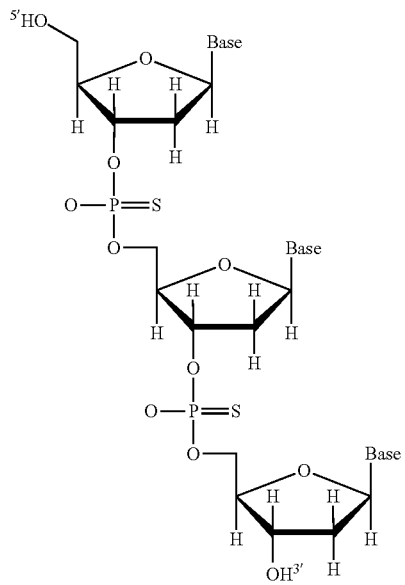

A further possibility for the prevention of exonucleic shortening can be achieved through the use of peptide nucleic acids (PNA).

An important component of this invention is that the nucleic acid used as "feed" during the PCR reaction has the ability to form double stranded structures itself or with other nucleic acid molecules present.

A further aspect of the present invention concerns the base sequence of the target substrate. There are several possible solutions for the base sequence of the oligonucleotides used as "feed". Both oligonucleotides that are complementary to a selected target sequence in the template nucleic acids used, and others with a more or less random sequence (so-called "random oligonucleotides") comprising the bases adenine (A), cytosine (C), guanine (G) and thymine (T) were tested successfully. Oligonucleotides that comprise, individually or in combination with A, C, G, T, one or more universal bases (e.g. inosine, 3-nitropyrrole or 5-nitroindole), one or more uracil, methylcytosine, base analogues or modified bases can also be used, as well as homo-oligomers consisting of a sequence of the same base (e.g. Oligo-dT), a universal base, a modified base or base analogue.

An important component of this invention is that complementary binding sites are available for the oligonucleotides used as "feed" in the PCR reaction. These binding sites can themselves be present on both the nucleic acids used as template and also on the oligonucleotides themselves used as "feed". This property is fulfilled by random oligonucleotides, for example, as they can find binding sites for every possible template nucleic acid and in addition can also form double stranded molecules with other random oligonucleotides.

The binding sites on which a double DNA strand is formed do not have to be perfectly complementary; bindings with one or more base mispairings may develop under typical PCR conditions, especially in the annealing stage. With oligonucleotides 20 or more bases in length in particular, the development of base mispairings is very likely.

Preferably, the "feed" oligonucleotide should have a length with which is possible to bind to a suitable opposite DNA strand under PCR conditions. Thus at the least, the oligonucleotide must have a length that allows an efficient binding in a PCR buffer at approx. 40° C.-90° C. Typically, binding should take place during the annealing stage of PCR, which is carried out mostly within a temperature range of approx. 45° C.-70° C. This results in a preferred length of the oligonucleotide of approx. 10 to approx. 100 bases, more preferably approx. 12 to approx. 80 bases, and especially approx. 20 to 45 bases. The preferred length selected depends, for example, on the sequence, the GC content and possibly other modifications of the oligonucleotide.

The preferred effective concentration of the "feed" oligonucleotide lies within a range of approx. 0.1 to approx. 20 μM, more preferably approx. 0.2 to approx. 2.5 μM, and especially approx. 0.5 to approx. 1.5 μM. The optimum concentration is co-determined by the other properties of the oligonucleotide, e.g. length and base sequence, since the efficiency of the binding to the opposite DNA strand is likewise affected by the concentration. For example, the preferred concentration for oligonucleotides with 20 to 45 bases of defined or random sequence (random oligonucleotides) lies between 0.2 and 2.5 μM.

Furthermore, the preferred effective concentration of the target substrate also depends on the concentration of the high fidelity DNA polymerase used. If it is thereby supposed, that 1 U of high fidelity DNA polymerase corresponds to approximately 1 pmol of polymerase molecules, then this gives a preferred ratio of high fidelity DNA polymerase molecules to "feed" oligonucleotide of between 1:1 and 1:1000, more preferably between 1:1 and 1:5000 and especially between 1:1 and 1:200. It is generally said that the ratio should be rather larger with a short feed oligonucleotide and rather smaller with a longer feed oligonucleotide. In either case care has to be taken that the number of feed oligonucleotide molecules and the ratio between high fidelity DNA polymerase molecules and "feed" oligonucleotide molecules is so selected that amplification is not inhibited.

The 5'-terminus of the "feed" oligonucleotide can be unmodified or additionally carry an modification. A 5'-modification is essentially unimportant within the meaning of this invention so long as the binding properties of the oligonucleotide to the template DNA and the binding of the high fidelity DNA polymerase are unimpeded. Possible modifications comprise C-linkers (e.g. C3-, C6-, C9-, C12-, C18-linkers), 5'-phosphate modifications, amino modifications, haptens incl. DIG, fluorescein, biotin, fluorescent dyes, quencher residues, thiol labels and other known 5'-modifications that do not impede or prevent the binding of the oligonucleotide and the high fidelity DNA polymerase to the template nucleic acid.

Internal modifications of the "feed" oligonucleotide are also possible and can be advantageous within the context of this invention. Internal modifications can involve the bases or the sugar-phosphate backbone. Modifications to the DNA backbone have already been discussed in the above section under the key term prevention of 3'-shortening by modification of the DNA backbone. In addition to the substitution of phosphate with phosphothioate in one, several or all positions of the DNA backbone mentioned there, all known changes of the backbone are possible so long as the binding of the high fidelity DNA polymerase to the template nucleic acid is not prevented completely. Moreover, the incorporation of abasic sites by a spacer is possible, or other modifications to bases, the backbone or side chains can be introduced. Locked nucleic acids, characterised in that they have a modified sugar, are mentioned here in particular.

A second important embodiment of the present invention concerns the use of double stranded oligonucleotides (also known as "hairpin oligonucleotides") as the target substrate.

These double stranded oligonucleotides are characterised in that they can form a double DNA strand using a self-complementary hairpin structure. The length and base sequence of the hairpin oligonucleotides are thereby so selected that they are present as double DNA strand at least during the annealing stage of PCR. The "feed" oligonucleotide added should preferably also be so constructed that it does not participate in the PCR reaction in any undesirable manner. Possible solutions as well as preferred basic properties of the "feed" oligonucleotide added are described in the following.

The "feed" oligonucleotide in its preferred embodiment should not be elongatable by DNA polymerase, that is should not be able to serve as a primer itself. This can be achieved by a modification of the 3'-terminus of the oligonucleotide, so that it cannot be elongated any further by the high fidelity DNA polymerase. This can be achieved in several ways. The modifications are preferably already incorporated during the DNA synthesis. Possible, suitable modifications include the incorporation of dideoxynucleotides, inverse bases, RNA, abasic sites, spacers, dyes, quencher residue, e.g. Black Hole Quencher, Dabcyl, minor groove binder, modified bases, e.g. super bases or halogenated bases or base analogues, and all other possible modifications to the sugar backbone and to the bases of the "feed" oligonucleotide as well as additional side groups that inhibit the ability of the high fidelity DNA polymerase to catalyse DNA synthesis. The preferred solution for the protection against elongation of the oligonucleotide is the incorporation of a 3'-phosphate group in place of the 3'-OH group required by the polymerase in the DNA oligonucleotide (see above).

The prevention of the 3'-shortening of the oligonucleotide is also possible through modification(s) of the DNA backbone. Owing to its 3'-5'-exonuclease activity, the high fidelity DNA polymerase has the ability to shorten such a primer at the 3'-terminus, whereby the modification to prevent unwanted 3'-elongation could undesirably be removed. This 3'-5'-exonucleolytic shortening can be impeded through one change or several changes in the backbone of the DNA. The preferred solution for this is the incorporation of at least one phosphothioate in the sugar-phosphate backbone of the DNA oligonucleotide in place of a phosphate. In order to prevent a complete 3'-5'-exonucleolytic shortening, it is sufficient to replace the phosphate in the backbone between the last and penultimate 3'-base of the DNA oligonucleotide with a phosphothioate. A further possibility for the prevention of exonucleolytic shortening can be achieved through the use of peptide nucleic acids (PNA).

Several solutions are also possible for the base sequence of the DNA oligonucleotide used as "feed". The preferred solution for hairpin oligonucleotides is the use of defined target sequences that can form a self-complementary hairpin structure. These oligonucleotides can carry several modifications both in the base sequence and in the backbone of the DNA. Thus the hairpin structure can comprise one or more base mispairings or abasic sites. Universal or modified bases could also be present in the DNA.

An important aspect of the present invention is that the oligonucleotides used as "feed" oligonucleotide during the PCR, have the ability to form double stranded structures that can serve as binding sites for the high fidelity polymerase. These binding sites can both arise by binding of the "feed" oligonucleotide to the nucleic acid used as a template, and be present on the hairpin oligonucleotide inserted as "feed" itself.

The binding sites on which a double DNA strand is formed do not have to be perfectly complementary; bindings with one or more base mispairings can also form. A "feed" oligonucleotide within the meaning of this invention should be able to form a double DNA strand at least during the annealing stage of PCR. Annealing is carried out mostly within a temperature range of approx. 45° C.-70° C. This gives rise to a preferred length of the self-complementary region of the hairpin structure of the oligonucleotide of approx. 10 to approx. 100 bases, more preferably approx. 12 to approx. 80 bases, and especially approx. 20 to 45 bases. The self-complementary region is a single stranded section of the oligonucleotide mentioned that can hybridise to a double strand with a more or less complementary structure of the same oligonucleotide. The preferred length selected depends, amongst other things, on the sequence, the GC content and other possible modifications of the oligonucleotide.

Preferably, the "feed" oligonucleotide should be of a length that, under PCR conditions, the binding of a double DNA strand or the binding to a suitable opposite DNA strand is possible. Thus at the least, the oligonucleotide should have a length that allows an efficient binding in a PCR buffer at approx. 40° C.-90° C. Typically, a binding in the annealing stage of PCR should take place, which is carried out mostly in a temperature range of approx. 45° C.-70° C. This gives rise to a preferred length of the self-complementary area of the hairpin structure of the oligonucleotide of approx. 10 to approx. 100 bases, more preferably approx. 12 to approx. 80 bases, and especially approx. 20 to 45 bases. The preferred length selected depends, for example, on the sequence, the GC content and possibly other modifications of the oligonucleotide.

The effective concentration of the "feed" oligonucleotide preferably lies within a range of approx. 0.05 to approx. 20 µM, 0.2 to 10 µM for example, and more preferably approx. 0.2 to approx. 2.5 µM. The optimum concentration is determined by the other properties of the oligonucleotide, e.g. length and base sequence. The preferred concentration for oligonucleotides comprising 20 to 45 bases of defined or random sequence (random oligonucleotides) lies between 0.2 and 2.5 µM. In addition, the effective concentration also depends on the concentration of high fidelity DNA polymerase. If it is thereby supposed, that 1 U of high fidelity DNA polymerase corresponds to approximately 1 pmol of polymerase molecules, This gives a preferred ratio of high fidelity DNA polymerase molecules to "feed" oligonucleotides of between 1:0.5 and 1:1000, for example between 1:1 and 1:5000, and especially between 1:1 and 1:200.

The 5'-terminus of the "feed" oligonucleotide can be unmodified or additionally carry an modification. A 5'-modification is essentially unimportant within the meaning of this invention so long as the binding properties of the oligonucleotide to the template DNA and the binding of the high fidelity DNA polymerase are not negatively affected. Possible modifications comprise C-linkers (e.g. C3-, C6-, C9-, C12-, C18-linkers), 5'-phosphate modifications, amino modifications, haptens incl. DIG, fluorescein, biotin, fluorescent dyes, quencher residues, thiol labels and other generally known 5'-modifications that do not impede the binding of the oligonucleotide and the high fidelity DNA polymerase to the template nucleic acid.

Internal modifications of the "feed" oligonucleotide are also possible and can be advantageous within the meaning of this invention. Internal modifications can affect both the bases and the sugar-phosphate backbone. Possible modifications of the DNA back bone have already discussed in more detail above. In addition to the mentioned exchange of phosphate by phosphothioate in one, several or all positions of the DNA backbone, other known changes of the backbone are also possible so long as the binding of the high fidelity DNA polymerase is not prevented completely. Moreover the incorporation of abasic sites by a spacer is possible or other modifications to bases, the backbone or side chains can be carried out. Locked nucleic acids, characterised in that they have a modified sugar, are mentioned here in particular. The incorporation of RNA is also possible.

A third important embodiment of the present invention concerns the use of any kind of double stranded "feed" DNA that does not carry the primer binding site of the end substance to be amplified. The length and base sequence of the "feed" DNA are thereby so selected that, at least during the annealing stage of PCR, it is present as double DNA strands. In addition, the "feed" DNA used should preferably be so constructed that it does not participate in the PCR reaction in any unwanted way and generates no by-products. Possible solutions as well as preferred basic properties of the "feed" DNA added are detailed in the following.

In the preferred embodiment the "feed" DNA should not be elongateable by the DNA polymerase, that is should not be able to serve as a primer itself. This can be achieved by modification of the 3'-end of the feed DNA, so that it cannot be elongated any further by the high fidelity DNA polymerase. There are several solutions for this, including the integration of dideoxynucleotides, inverse bases, RNA, abasic sites, spacers, colourings, quencher residues, e.g. Black Hole Quencher, Dabcyl, minor groove binders, modified bases, e.g. super bases or halogenised bases or base analogues, abasic sites, blocking the 3'-OH group (e.g. substitution by phosphate) as well as all other possible modifications to the sugar backbone, and to the bases and additional side groups that inhibit the ability of the high fidelity DNA polymerase to catalyse DNA synthesis. This can also be carried out, for example, by enzymatic or chemical modification. A further possibility is the use of circular DNA molecules as "feed" DNA. This circular DNA can be, for example, a plasmid DNA, or can be smaller, synthetically prepared ring-shaped DNA molecules.

Owing to its 3'5'-exonuclease activity, the high fidelity DNA polymerase has the ability to shorten a "feed" DNA at the 3'-end, whereby the modification to prevent unwanted 3'-extension could be undesirably removed. This 3'-5'-exonucleolytic shortening can be impeded through changes in the backbone of the DNA. The preferred solution for this is again the incorporation of at least one phosphothioate in place of a phosphate in the sugar-phosphate backbone of the DNA oligonucleotide. In order to prevent a complete 3'-5'-exonucleolytic shortening, it is sufficient to replace the phosphate in the backbone between the last and penultimate 3'-base of the DNA oligonucleotide with a phosphothioate. A further possibility for the prevention of exonucleolytic shortening can be achieved through the use of peptide nucleic acids (PNA).

According to a further preferred aspect, the "feed" DNA should comprise a group of DNA molecules with as many different sequence motifs as possible. In this way sufficient suitable binding sites are always present in any template nucleic acid used, which is advantageous for the generic usability of the selected "feed" DNA. The "feed" DNA can carry several modifications, both to the DNA bases and also in the backbone of the DNA. Universal or modified bases can also be present, or modifications to the side chains inserted.

An important aspect of this invention is that, as already mentioned above, the DNA inserted as "feed" DNA during the PCR reaction has the ability to form double stranded structures with other "feed" DNA molecules or the template DNA. These double stranded structures serve as binding sites for the high fidelity DNA polymerase. The binding sites can both arise by binding of the "feed" oligonucleotide to the nucleic acid used as a template and be present on the hairpin oligonucleotide used as "feed" itself.

The base sequence of the "feed" DNA used should preferably be so constructed that no generally occurring by-products are detectable in disruptive quantity through presence of the "feed" DNA, or the feed DNA per se is detectable. A disruptive quantity is generally reached when the by-products generated are detectable as background in the PCR product analytical methods used, or they show a disruptive impact on subsequent applications, e.g. cloning, in vitro transcription/translation or mutagenesis.

The binding sites on which a double DNA strand is formed do not have to be perfectly complementary; bindings with one or more base mispairings can also form. A "feed" DNA within the meaning of this invention should preferably be able to form a double DNA strand at least during the annealing stage of PCR. Annealing is carried out mostly within a temperature range of approx. 45° C.-70° C. This gives rise to a preferred length of the "feed" DNA of approx. 12 bp to approx. 1000 bp. The preferred length selected depends on the sequence, the GC content and possibly other modifications of the "feed" DNA.

Preferably, the "feed" DNA should be of a length that, under PCR conditions, the binding of a double DNA strand or binding to a suitable opposite DNA strand is possible. Thus at the least, the oligonucleotide must have a length that allows an efficient binding in a PCR buffer at approx. 40° C.-90° C. Typically, a binding in the annealing stage of PCR should take place, which is carried out mostly in a temperature range of approx. 45° C.-70° C. This gives rise to a preferred length of the "feed" DNA of at least approx. 12 bases to several 1000 bases (for example approx. 2000, 3000, 4000, 5000 or 10,000 bases). The preferred length selected also depends, amongst other things, on the sequence, the GC content and possibly other modifications of the "feed" DNA.

The optimum concentration is determined by the length and base sequence as well as the other properties of the "feed" DNA. The preferred concentration for "feed" DNA with approx. length of 12 bp to approx. 1000 bp lies between 0.2 µM and 2.5 µM. In addition, the effective concentration also depends on the concentration of the high fidelity DNA polymerase. If it is thereby supposed, that 1 U of high fidelity DNA polymerase corresponds to approximately 1 pmol of polymerase molecules, this gives rise to preferred ratio of high fidelity DNA polymerase molecules to "feed" oligonucleotides between 1:0.5 and 1:1000, between 1:1 and 1:5000 for example, and especially between 1:1 and 1:200.

The 5'-terminus of the "feed" DNA can be unmodified or additionally carry a modification. A 5'-modification is essentially unimportant within the meaning of this invention so long as the binding properties of the oligonucleotide to the template DNA and the binding of the high fidelity DNA polymerase are not impaired. Possible modifications comprise C-linkers (e.g. C3-, C6-, C9-, C12-, C18-linkers), 5'-phosphate modifications, amino modifications, haptens incl. DIG, fluorescein, biotin, fluorescent dyes, quencher residues, thiol labels and other known 5'-modifications that do not prevent the binding of the "feed" DNA and the high fidelity DNA polymerase.

Internal modifications of the "feed" DNA are also possible and can be advantageous within the meaning of this invention. Internal modifications can affect the bases or the sugar-phosphate backbone. Possible modifications of the DNA back bone have already been discussed in more detail above. In addition to the mentioned substitution of phosphate by phosphothioate in one, several or all positions of the DNA backbone, known changes of the backbone known from the state of the art are possible, so long as the binding of the high fidelity DNA polymerase to the double DNA strand is not prevented. Moreover the incorporation of abasic sites by a spacer or other modifications to bases, the backbone or side chains are possible. Locked nucleic acids are mentioned here especially, characterised in that they have a modified sugar. The incorporation of RNA is also feasible.

Finally, a fourth preferred embodiment of the invention concerns the addition of RNA as a target substrate or "feed" to a PCR.

A further possible solution within the meaning of the invention is the addition of RNA to the PCR by means of a high fidelity DNA polymerase. Surprisingly, the addition of RNA to the PCR by means of a high fidelity DNA polymerase shows the desired positive effect of the improvement of sensitivity in the PCR within the meaning of the invention. The most probable mechanism is the formation of double stranded RNA-DNA hybrids, which can be recognised by the high fidelity DNA polymerase. The recognition of RNA-DNA double strands by the high fidelity DNA polymerase is also conceivable. The length and base sequence of the "feed" RNA are thereby so selected that it has the ability, at least during the annealing stage of the PCR, to form a double stranded structure. In addition, the "feed" RNA added can be so constructed that it does not participate in the PCR reaction in unwanted ways and produces no by-products. It is not however essential that such a modification achieves an improvement of PCR yield and sensitivity within the meaning of the invention. Possible technical solutions as well as basic properties of the "feed" RNA added are detailed in the following.

It is not to be expected that the "feed" RNA itself can serve as primer or template for the high fidelity DNA polymerase. Modifications to the 3'-terminus of the feed RNA are therefore, within the meaning of this invention, not essential, but can be carried out. Several solutions are suitable for this, whereby the modifications are preferably produced by enzymatic or chemical processes. These include the incorporation of dideoxynucleotides, inverse bases, spacers, dyes, quenchers, e.g. Black Hole Quencher, Dabcyl, minor groove quencher residues, modified bases, e.g. super bases, halogenated bases or base analogues, abasic sites, incorporation of DNA with a blocked 3'-OH group (e.g. replacement of the 3'-OH group by phosphate) as well as all other known modifications to the sugar backbone, e.g. 2-O-methyl RNA, and to the bases, as well as additional side groups that inhibit the ability of the high fidelity DNA polymerase to catalyse DNA synthesis. This can be achieved by enzymatic or chemical modification. A further possibility is the use of circular RNA molecules as "feed" RNA. This can be, for example, smaller, synthetically produced ring-shaped RNA molecules.

Therefore, the "feed" RNA should preferably comprise a group of RNA molecules with as many different sequence motifs as possible. Thus, sufficient suitable binding sites are always available in any template nucleic acid used, which is advantageous for the generic usability of the selected "feed" RNA. Surprisingly, a comparable effect to RNA homopolymers could also be achieved (poly-A RNA, see example 8). The "feed" RNA can carry several modifications both to the bases and in the sugar-phosphate backbone. Universal or modified bases can also be present, or modifications to the side chains inserted.

A fundamental aspect of this invention is that the RNA inserted as "feed" RNA during the PCR reaction has the ability to form double stranded structures with itself or other nucleic acid molecules present. The base sequence of the "feed" RNA used should be so constructed so that no general occurring by-products are formed in disruptive amounts through presence of the "feed" RNA, or the feed RNA per se is detectable. A disruptive amount is generally reached when the by-products generated are detectable as background in the PCR product analytical methods use, or they show a disruptive impact on subsequent applications, e.g. cloning, in vitro transcription/translation or mutagenesis.

The binding sites on which a double strand is formed do not have to be perfectly complementary; bindings with one or more base mispairings may also form. A "feed" RNA within the meaning of this invention should preferably be able to form a double strand at least during the annealing stage of PCR. Annealing is carried out mostly within a temperature range of approx. 45° C.-70° C. This gives rise to a preferred length of the "feed" RNA arises of approx. 12 bases to several 1000 bases (e.g. 2000, 3000, 4000, 5000 or 10,000 bases). The preferred length selected depends on the sequence, the GC content and possibly other modifications of the "feed" RNA.

Preferably, the "feed" RNA should be of a length that, under PCR conditions, the binding of a double strand or binding to a suitable opposite strand is possible. Thus at the least, the oligonucleotide must have a length that allows an efficient binding in a PCR buffer at approx. 40° C.-90° C. Typically, a binding in the annealing stage of PCR should take place, which is carried out mostly in a temperature range of approx. 40° C.-70° C. This gives rise to a preferred length of the "feed" RNA arises of at least approx. 12 bases to several 1000 bases (approx. 2000, 3000, 4000, 5000 or 10,000 bases). The preferred length selected also depends, amongst other things, on the sequence, the GC content and possibly other modifications of the "feed" RNA.

The effective concentration of the "feed" RNA preferably lies within a range of approx. 0.04 and 40 ng/µl. The optimum concentration is determined by the length and base sequence as well as the other properties of the "feed" RNA. The preferred concentration for a "feed" RNA with a length of approx. 12 bases to approx. 10,000 bases lies between 0.04 ng/µl bis 40 ng/µl.

The 5'-terminus of the "feed" RNA can be unmodified or additionally carry an modification. A 5'-modification is essentially unimportant within the meaning of this invention so long as the binding properties of the "feed" RNA are not affected so that the binding of the high fidelity DNA polymerase is prevented. Suitable modifications comprise C-linkers (e.g. C3-, C6-, C9-, C12-, C18-linkers), 5'-phosphate modifications, amino modifications, haptens incl. DIG, fluorescein, biotin, fluorescent dyes, quencher residues, thiol labels and other known 5'-modifications that do not prevent the binding of the high fidelity DNA polymerase.

Internal modifications of the "feed" RNA are also possible and can be advantageous within the meaning of this invention. Internal modifications can affect the bases, the sugar-phosphate backbone or inserted side chains. Generally all known changes of the RNA backbone are conceivable, so long as the binding of the "feed" RNA or the high fidelity DNA polymerase is not prevented.

Figure 1:
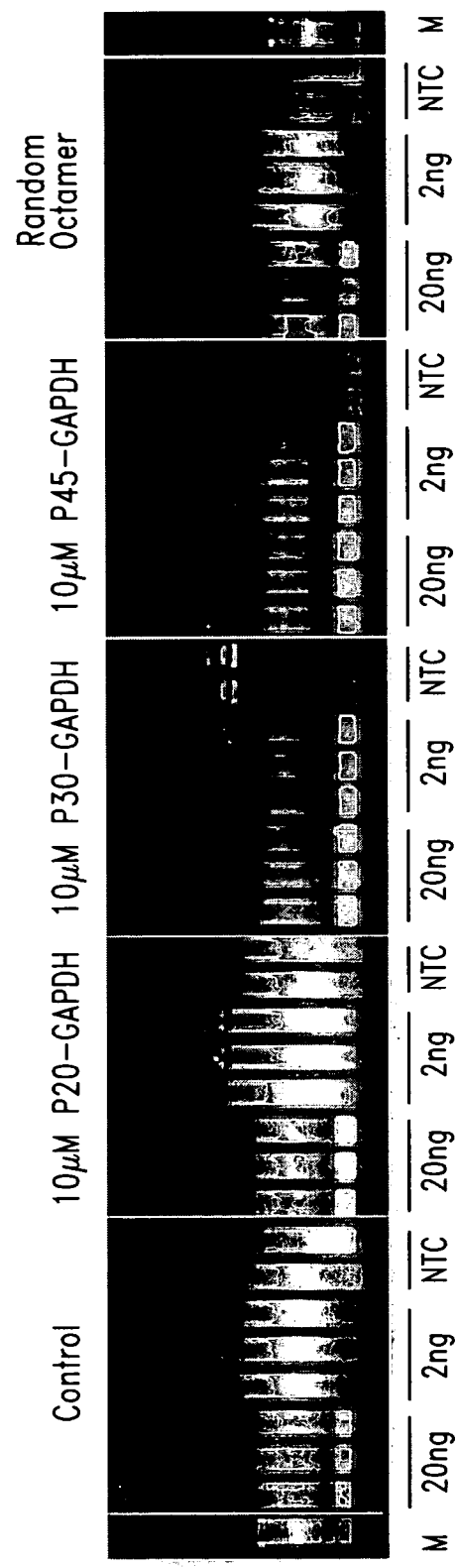
FIG. 1 an agarose gel analysis of a PCR to investigate of the effects of "feed" nucleotides of different lengths on the PCR amplification of ERCC1.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

The invention is illustrated in detail by means of embodiment examples subsequently.

EXAMPLE 1

In this example, the effect of "feed" oligonucleotides of different lengths (P20-GAPDH; P30-GAPDH; P45-GAPDH and random octamer) on the PCR amplification of ERCC1 by means of high fidelity DNA polymerase is investigated. The oligonucleotides P20-GAPDH (20-mer); P30-GAPDH (30-mer); and P45-GAPDH (45-mer) are complementary to the human GAPDH gene locus. These are single stranded oligonucleotides with natural sugar-phosphate backbone, which carry a 3'-phosphate instead of the 3'-OH end group. The random octamer is an 8-mer with a random sequence ($N_8$). This is likewise a single stranded oligonucleotide with natural sugar-phosphate backbone and a 3'-OH group.

The design and procedure of the high fidelity PCR were as follows. ProofStart DNA polymerase (QIAGEN GmbH, Hilden Germany; catalogue number 202205) was used for the PCR reactions. Each reaction assay comprised 1× ProofStart PCR buffer, 1.25 U of ProofStart DNA polymerase, 1 µM of ERCC1 forward and 1 µM of reverse primer and 0.3 mM each of dNTPs (dATP, dCTP, dGTP, dTTP) in a reaction volume of 25 µl. In triplicate assays (that is, three parallel experiments) 20 ng or 2 ng of human genomic DNA was added in each case and in duplicate assays (that is, two parallel experiments) a comparable quantity of water was added as a negative control (NTC: "no template control"). In addition, one of the oligonucleotides P20-GAPDH; P30-GAPDH; P45-GAPDH were added as "feed" oligonucleotides within the meaning of the invention as well as a "random octamer" in a concentration of 10 µM in each case. As a control, corresponding reactions were carried out in each case without "feed" oligonuceotides (caption: "control" in FIG. 1).

The PCR protocol comprised an initial reactivation of the ProofStart DNA polymerase ("Hot Start") for 5 min at 95° C., followed by 35 cycles of 30 sec at 94° C., 60 sec at 61° C. and 1 min 30 sec at 72° C., as well as a concluding stage of 10 min at 72° C. ("final extension"). The following sequences of oligonucleotides and primers are stated in the 5'-3' direction.

```
ERCC1-for:
                                            (SEQ ID NO:1)
GCT GTT TGA TGT CCT GCA CGA G ERCC1-rev:
                                            (SEQ ID NO:2)
GCC TGG CCT GGG AGG ACG ATT
```

Sequences of the "Feed" Oligonucleotides:

```
P20-GAPDH:
                                            (SEQ ID NO:3)
GCG TCA AAG GTG GAG GAG TG [Phosp-Q]

P30-GAPDH:
                                            (SEQ ID NO:4)
GCG TCA AAG GTG GAG GAG TGG GTG TCG CTG [Phosp-Q]

P45-GAPDH:
                                            (SEQ ID NO:5)
GCG TCA AAG GTG GAG GAG TGG GTG TCG CTG TTG AAG
TCA GAG GAG [Phosp-Q]
[Phosp-Q]:3'-phosphate instead of 3'-OH)

Random octamer: NNN NNN NN
```

10 µl of each PCR was analysed on an ethidium bromide stained agarose gel (2%). A 100 bp ladder (Invitrogen GmbH, Karlsruhe, Germany, 15628-050) served as a size standard. FIG. 1 shows an agarose gel analyse of the PCR with respect to the effect of "feed" oligonucleotides of different lengths (P20-GAPDH; P30-GAPDH; P45-GAPDH and random octamer) on the PCR amplification of ERCC1. M=marker.

It can be seen from FIG. 1 that an improvement in the yield using 20 ng of template DNA can be observed under all conditions in comparison to the control. A successful amplification, that is an improvement of the sensitivity by a factor of 10, was achieved using the "feed" oligonucleotides P30-GAPDH (30 mer) and P45-GAPDH (45 mer). At the same time, the background often appearing as "smear" in the high fidelity PCR reactions was also clearly reduced.

In conclusion, this suggests that oligonucleotides which have the ability to form a double DNA strand under PCR conditions because of their melting point (owing to length and GC content) are especially suitable as "feed oligonucleotides" within the meaning of the invention.

EXAMPLE 2

In this example, the effect of hairpin "feed" DNA oligonucleotides P78 3'P and P78 3'P-Thio on the PCR with high fidelity DNA polymerase was investigated. The oligonucleotides comprise a sequence in their 5'-region which is complementary to the human GAPDH gene locus. The 3'-region is complementary to the 5'-region of the oligonucleotide so that a double stranded hairpin structure can be formed. These are oligonucleotides which carry a 3'-phosphate instead of a 3'-OH group. The oligonucleotide P78 3'P-Thio carries a phosphothioate in the sugar-phosphate backbone of the DNA between the last and penultimate 3'-base.

The design and procedure of PCR by means of high fidelity DNA polymerase were as follows. ProofStart DNA polymerase (QIAGEN GmbH, Hilden Germany; catalogue number 202205) was used for the PCR reactions. Each reaction assay comprised 1× ProofStart PCR buffer, 1.25 U of ProofStart DNA polymerase, 1 µM of forward and 1 µM of reverse primer for CFTR (CYST) and 0.3 mM each of dNTPs (dATP, dCTP, dGTP, dTTP) in a reaction volume of 25 µl. In duplicate assays (that is, two parallel experiments) 25 ng, 5 ng or 1 ng of human genomic DNA was added in each case and in a single assay a comparable quantity of water was added as a negative control (NTC: "no template control"). In addition, one of the oligonucleotides P78 3'P and P78 3'P-thio were added in each case as "feed" oligonucleotides within the meaning of the invention in a concentration of 2.5 µM, 1 µM, 0.5 µM and 0.2 µM respectively. As a control, corresponding reactions were carried out in each case without "feed" oligonuceotides (caption in FIG. 2: "control"). The samples were cooled during the preparation of the PCR.

The PCR protocol comprised an initial reactivation of the ProofStart DNA polymerase ("Hot Start") for 5 min at 95° C., followed by 35 cycles of 30 sec at 94° C., 60 sec at 61° C. and 1 min 30 sec at 72° C., as well as a concluding stage of 10 min at 72° C. ("final extension"). The following sequences of oligonucleotides and primers are stated in the 5'-3' direction. PCR Primer Sequences:

```
CYST 3:
                                            (SEQ ID NO:6)
CCC AAA CCC AAC CCA TAC ACA C
```

CYST 5:
(SEQ ID NO:7)
CCT TGC CTT AGA TGT GTC GGC A

Sequences of the "Feed" Oligonucleotides:

P78 3'P:
(SEQ ID NO:8)
GCG TCA AAG GTG GAG GAG TGG GTG TCG CTG TTG AAG

TCA TGA CTT CAA CAG CGA CAC CCA CTC CTC CAC CTT

TGA CGC [Phosp-Q]
([Phosp-Q]:3'-phosphate instead of 3'-OH)

P78 3'P-thio:
(SEQ ID NO:9)
GCG TCA AAG GTG GAG GAG TGG GTG TCG CTG TTG AAG

TCA TGA CTT CAA CAG CGA CAC CCA CTC CTC CAC CTT

TGA CG*C [Phosp-Q]
([Phosp-Q]:3'-phosphate instead of 3'-OH;
*:phosphothioate in the backbone)

10 μl of each PCR reaction was analysed on an ethidium bromide stained agarose gel (1%). A 100 bp ladder (Invitrogen, 15628-050) served as a size standard.

Figure 2:
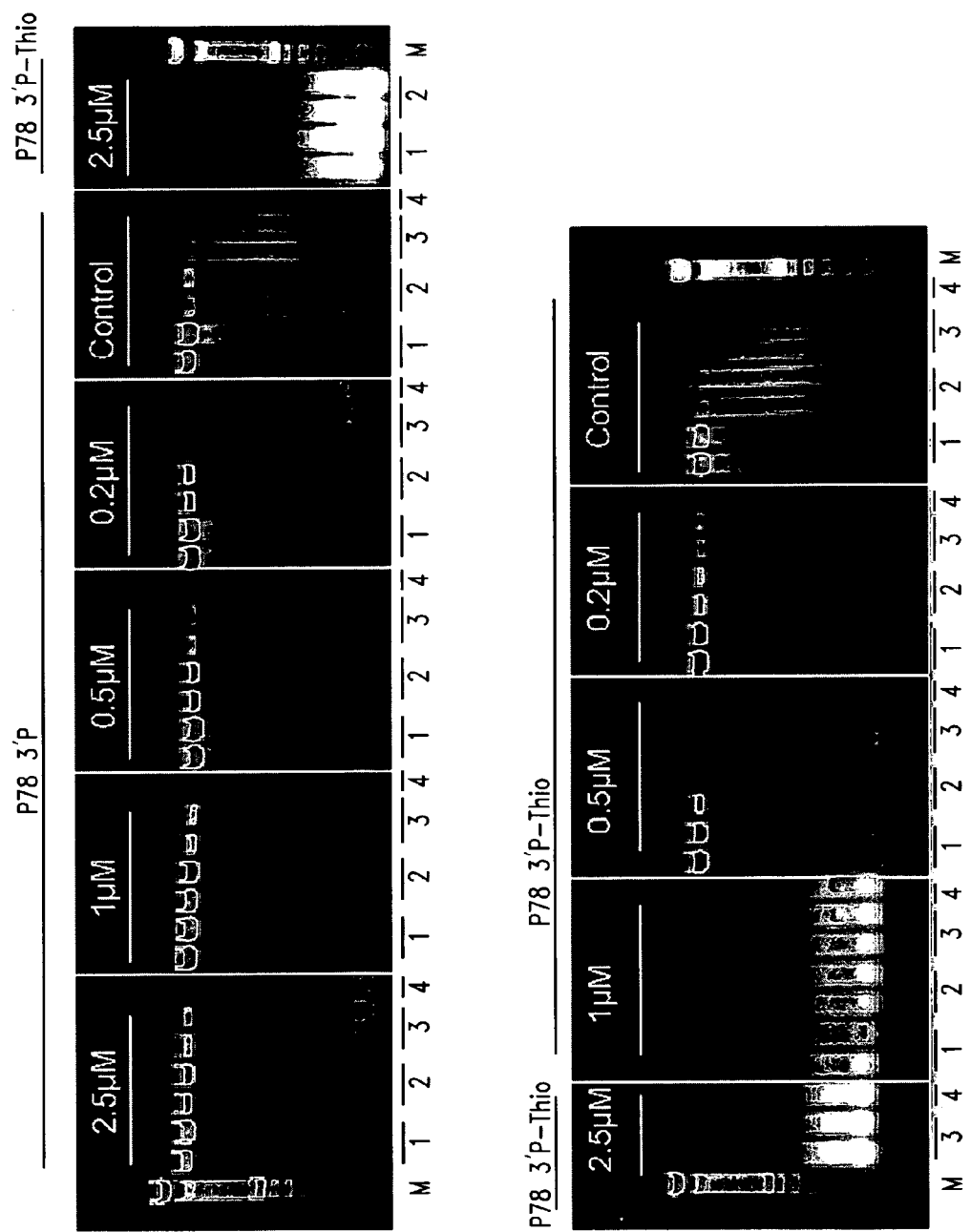
FIG. 2 an agarose gel analysis of a PCR to investigate the effects of hairpin "feed" oligonucleotides on the PCR amplification of a 1.5 kb fragment from the human CFTR gene locus.

FIG. 2 shows the agarose gel analysis of the PCR to investigate the effect of hairpin "feed" oligonucleotides (P78 3'P, P78 3'P-Thio) on the PCR amplification of a 1.5 kb fragment from the human CFTR gene locus. Trace 1: 25 ng HuDNA; Trace 2: 5 ng HuDNA; Trace 3: 1 ng HuDNA; Trace 4: NTC; M=marker.

It is apparent from FIG. 2 that through the addition of the hairpin "feed" DNA oligonucleotides P78 3'P and P78 3'P-Thio, the yield and sensitivity of the high fidelity PCR of the 1.5 kb fragment could be clearly increased in comparison to the control without "feed" DNA oligonucleotides. At the same time, the background often appearing as "smear" in the high fidelity PCR reactions was also clearly reduced. The "feed" DNA oligonucleotide P78 3'P had a positive effect on yield and sensitivity of the high fidelity PCR amplification of the 1.5 kb fragment over the whole range tested of 0.2 μM to 2.5 μM.

The "feed" DNA oligonucleotide P78 3'P-Thio showed a positive effect within a range of 0.2 μM to 0.5 μM in the amplification of the 1.5 b fragment. At higher concentrations only the hairpin "feed" DNA oligonucleotide was detectable on the gel as a smear at 200 bp. This effect did not occur with the "feed" DNA oligonucleotide P78 3'P.

In conclusion, this suggests that the "feed" DNA oligonucleotide P78 3'P is degraded by the 3'-5'-exonuclease activity of the high fidelity DNA polymerase. Thereby it is possible to use considerably higher concentrations of "feed" DNA oligonucleotide P78 3'P compared to P78 3'P-Thio. By combining 3'-phosphate with a phosphothioate, as with P78 3'P-Thio, the "feed" DNA oligonucleotide remains clearly intact and thus has the ability to bind the high fidelity DNA polymerase during the whole PCR.

EXAMPLE 3

In this example, the effect of "feed" oligonucleotides which comprise a randomised part or the universal base inosine (N14-degAATAAA; pA-I; βActpA-6I-3') on the PCR amplification of a 1.5 kb fragment from the human CFTR gene locus was investigated.

The oligonucleotides N14-degAATAAA, pA-I, and βActpA-6I-3' (for sequences see below) were tested for their performance in the PCR. These are single stranded oligonucleotides with natural sugar-phosphate backbone which carry a 3'-OH end group.

The design and procedure of PCR by means of DNA polymerase were as follows. ProofStart DNA polymerase (QIAGEN, catalogue number 202205) was used for the PCR reactions. Each reaction assay comprised 1× ProofStart PCR buffer, 1.25 U of ProofStart DNA polymerase, 1 μM each of forward and reverse primer and 0.3 mM each of dNTPs (dATP, dCTP, dGTP, dTTP) in a reaction volume of 25 μl. In duplicate assays 25 ng, 5 ng or 1 ng of human genomic DNA were added and in a single assay a comparable quantity of water was used as a negative control (NTC: "no template control"). In addition, one of the oligonucleotides N14-degAATAAA, pA-I and βActpA-6I-3' were added in each case as "feed" oligonucleotides within the meaning of the invention in a concentration of 10 μM. As a control, corresponding reactions were carried out in each case without "feed" oligonuceotides (caption in FIG. 3: "control"). The samples were cooled during the preparation of the PCR.

The PCR protocol comprised an initial reactivation of the ProofStart DNA polymerase ("Hot Start") for 5 min at 95° C., followed by 35 cycles of 30 sec at 94° C., 60 sec at 61° C. and 1 min 30 sec at 72° C., as well as a concluding stage of 10 min at 72° C. ("final extension"). The following sequences of oligonucleotides and primers are stated in the 5'-3' direction.

PCR Primer Sequences:

CYST 3:
(SEQ ID NO:6)
CCC AAA CCC AAC CCA TAC ACA C

CYST 5:
(SEQ ID NO:7)
CCT TGC CTT AGA TGT GTC GGC A

Sequences of the "Feed" Oligonucleotides:

N14-degAATAAA:
(SEQ ID NO:10)
NNN NNN NNN NNN NNH HND DVA ATA AA pA-I:
(SEQ ID NO:11)
III III III III III III III AAT AAA βActpA-6I-3':
(SEQ ID NO:12)
GTA CAC TGA CTT GAG ACC AGT TGA ATA AAI III II In the sequence of N14-degAATAAA, H refers to A or C or T; D refers to A or G or T; and V refers to A or C or G.

10 μl of each PCR reaction was analysed on an ethidium bromide stained agarose gel (2%). A 100 bp ladder (Invitrogen, 15628-050) served as a size standard.

Figure 3:
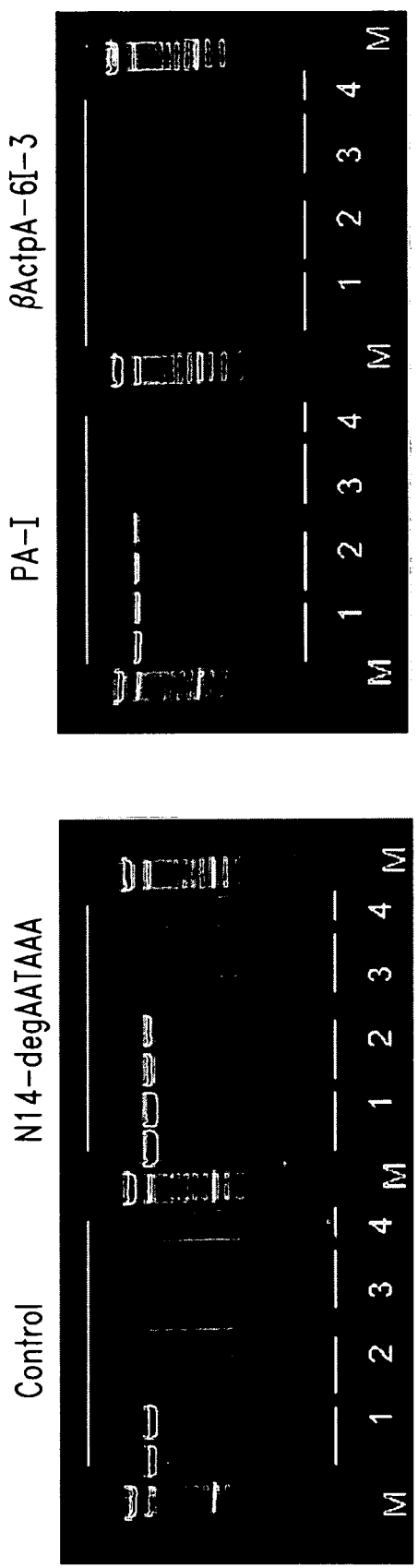
FIG. 3 an agarose gel analysis of PCR products to investigate the effects of "feed" oligonucleotides of different lengths on the PCR amplification of a 1.5 kb fragment from the human CFTR gene locus.
Figure 4A:
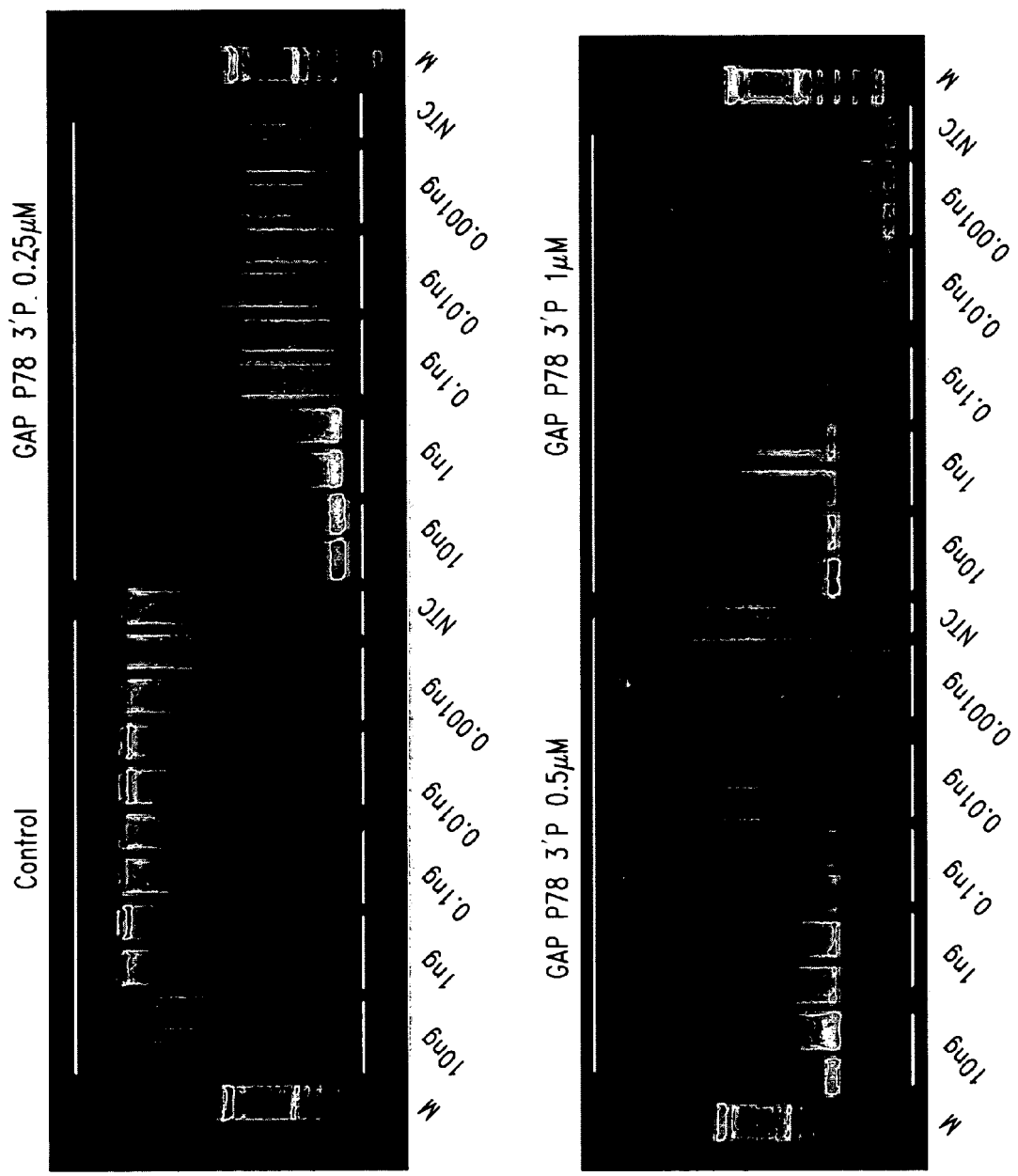
FIG. 4A to 4D agarose gel analyses of PCR products to investigate the effects of oligonucleotides with different properties on the PCR amplification of β-actin.
Figure 4B:
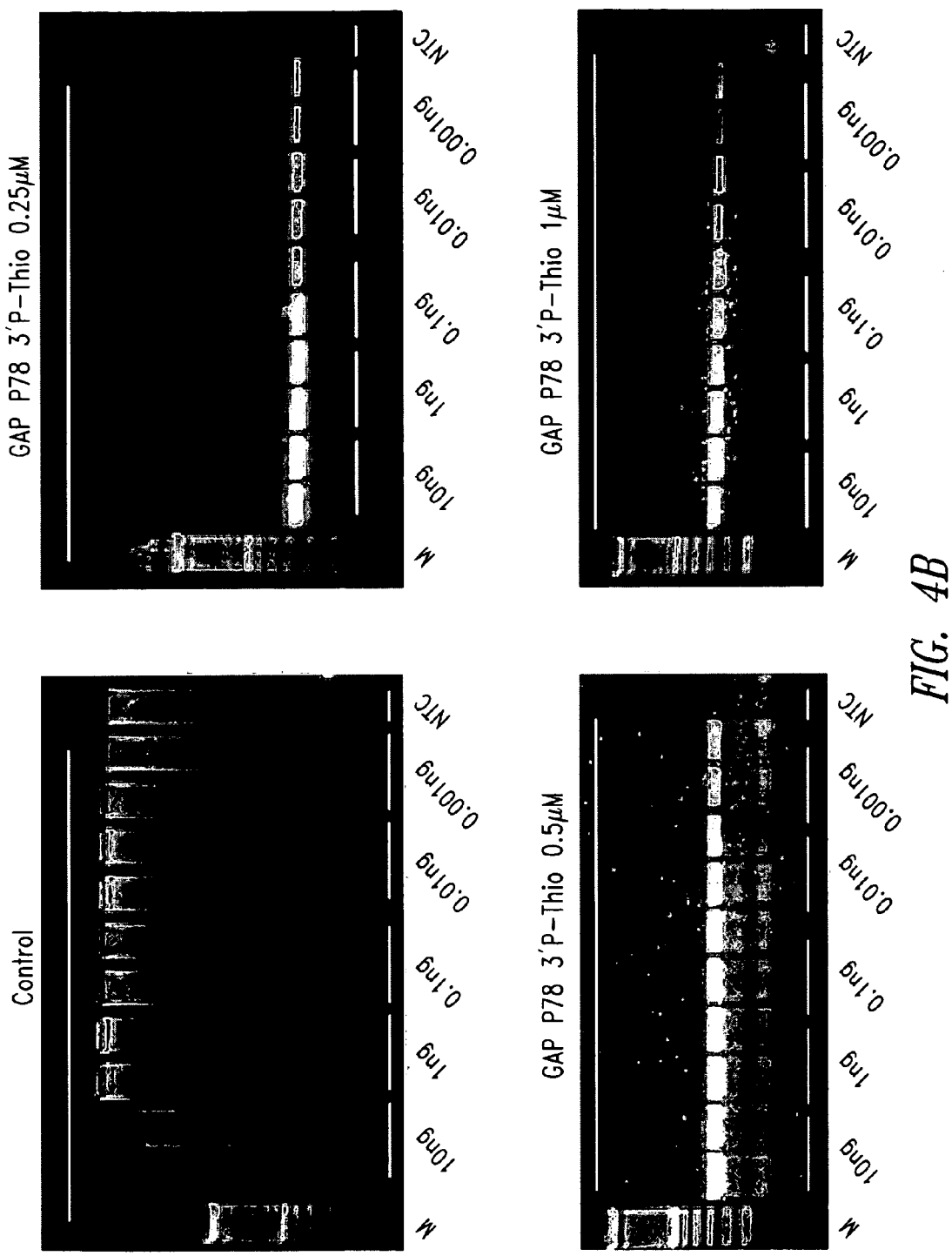
Figure 4C:
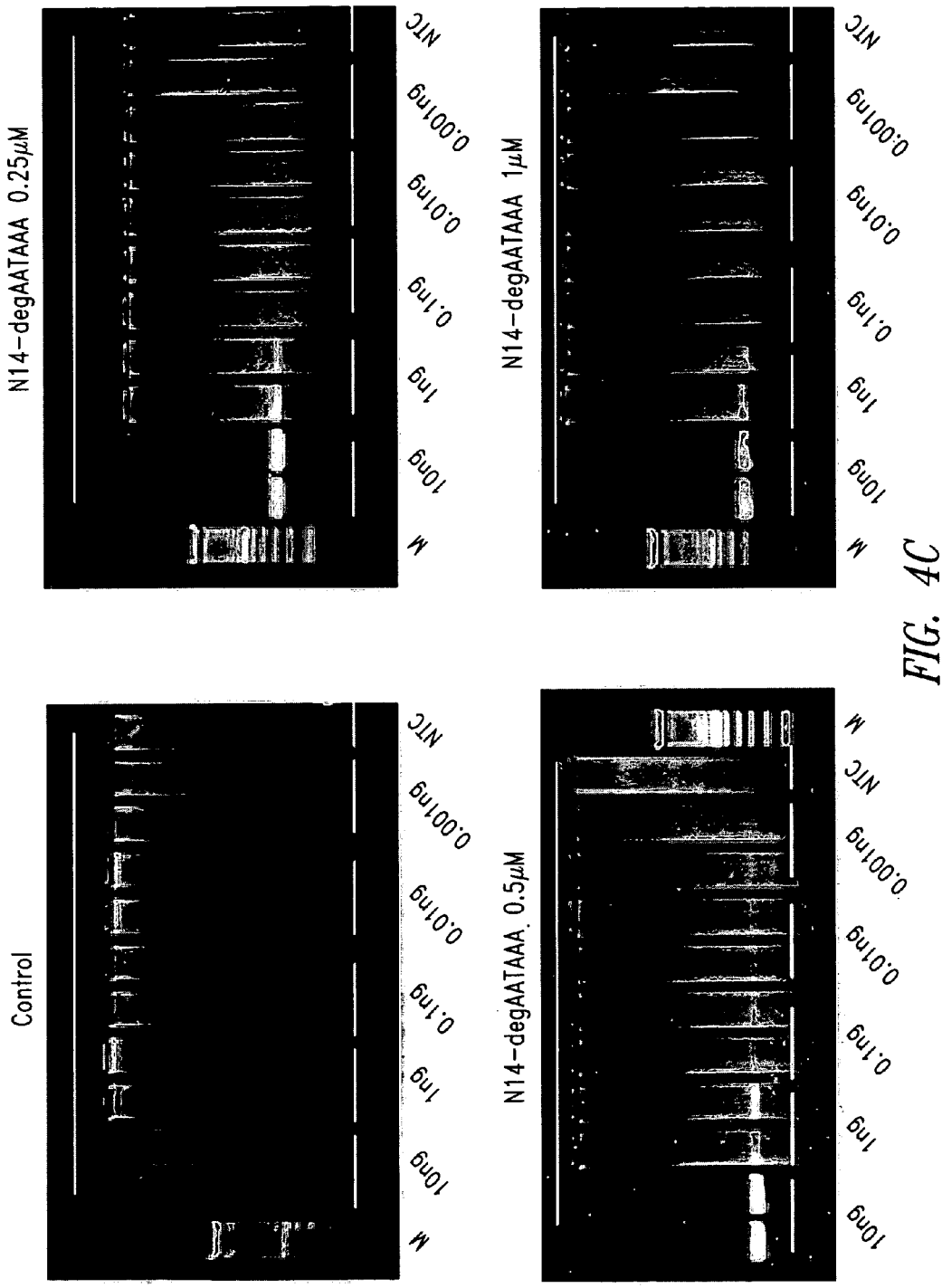
Figure 4D:
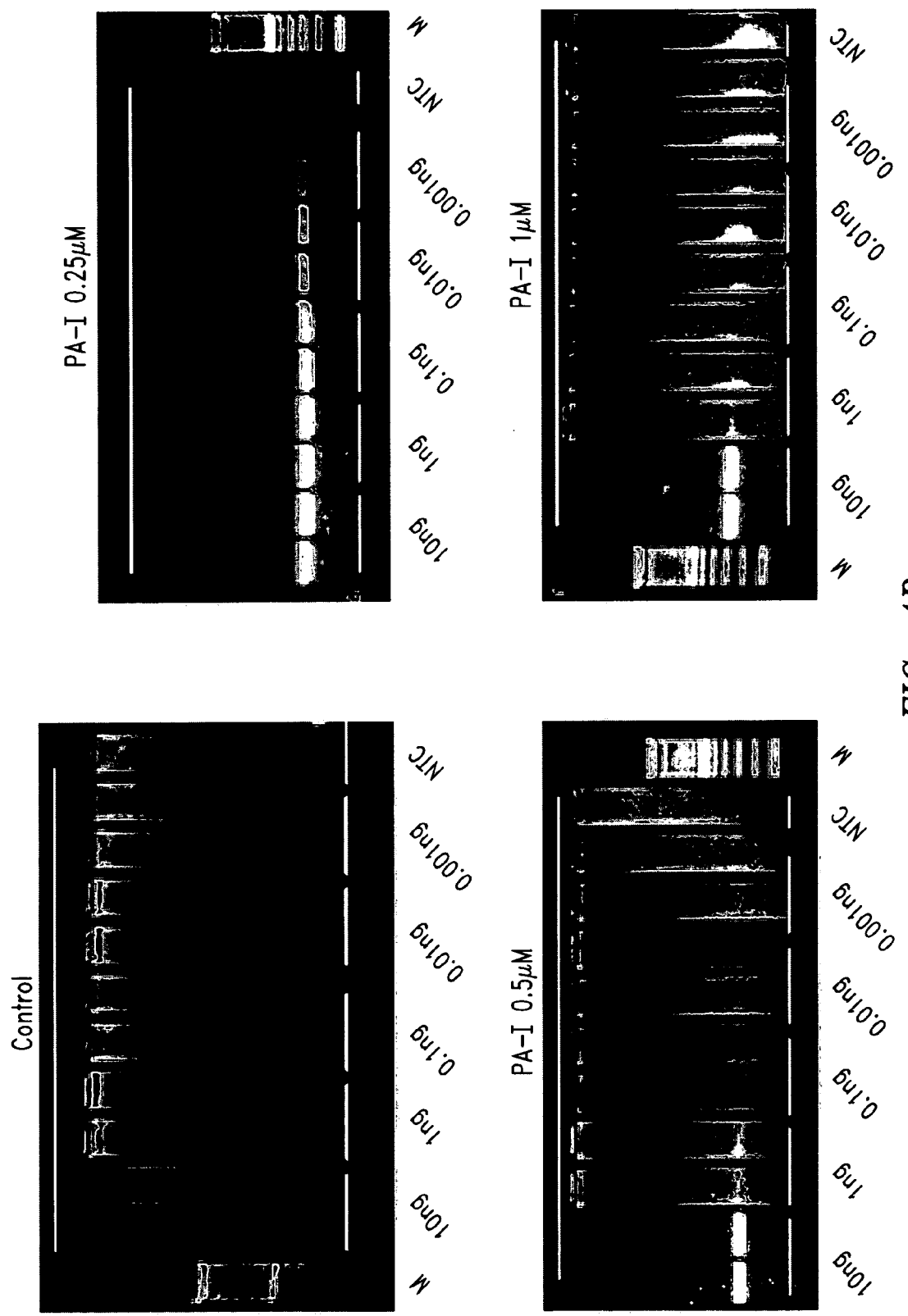

FIG. 3 shows the agarose gel analysis of the PCR products to investigate the effect of "feed" oligonucleotides of different lengths (N14-degAATAAA; pA-I; βActpA-6I-3') on the PCR amplification of a 1.5 kb fragment from the human CFTR gene locus. Trace 1: 25 ng HuDNA; Trace 2: 5 ng HuDNA; Trace 3: 1 ng HuDNA; Trace 4: NTC; M=marker.

By addition of the "feed" DNA oligonucleotides N14-degAATAAA and pA-I the yield and sensitivity of the high fidelity PCR can be clearly increased in comparison to the control without "feed" DNA oligonucleotides. At the same time, the background often appearing as "smear" in the high fidelity PCR reactions was also clearly reduced.

The "feed" DNA oligonucleotide βActpA-6I-3' with 6 inosine bases on the 3'-end is not suitable as a "feed" DNA oligonucleotide.

In conclusion, this suggests that oligonucleotides with randomised sequences or universal bases can be used effectively as "feed" DNA oligonucleotides. Also, use of standard oligonucleotides unprotected from degradation by the 3'-5'-exonuclease activity of the polymerase used as "feed" DNA oligonucleotides is feasible.

EXAMPLE 4

In this example, the effect of "feed" DNA oligonucleotides with different properties on the PCR with high fidelity DNA polymerase was investigated. The oligonucleotides GAP P78 3'P, GAP P78 3'P-Thio, N14-degAATAAA and PA-I with the sequences stated below were added to the PCR. The oligonucleotides GAP P78 3'P and GAP P78 3'P-Thio have already been described in example 2 and the oligonucleotides N14-degAATAAA and PA-I were already described in example 3.

The design and procedure of the high fidelity PCR were as follows. ProofStart DNA polymerase (QIAGEN, catalogue number 202205) was used for the PCR reactions. Each reaction assay comprised 1× ProofStart PCR buffer, 1 U of ProofStart DNA polymerase, 1 µM each of β-Actin forward and reverse primer and 0.3 mM each of dNTPs (dATP, dCTP, dGTP, dTTP) in a reaction volume of 20 µl.

In duplicate assays 10 ng, 1 ng, 0.1 ng, 0.01 ng and 0.001 ng of K562 cDNA (from K562 cells, see general methods at the end of the examples) were added in each case and likewise a comparable quantity of water was added to another duplicate assay as a negative control (NTC: "no template control"). In addition, the oligonucleotides GAP P78 3'P, GAP P78 3'P-Thio, N14-degAATAAA and PA-I were added in each case as "feed" within the meaning of the invention in a concentration of 0.25 µM, 0.5 µM and 10 µM. As a control, corresponding reactions were carried out in each case without "feed" oligonuceotides (caption in FIG. 4A to 4D: control). The samples were cooled during the preparation of the PCR.

The PCR protocol comprised an initial reactivation of the ProofStart DNA polymerase ("Hot Start") for 5 min at 95° C., followed by 35 cycles of 30 sec at 94° C., 60 sec at 61° C. and 1 min 30 sec at 72° C., as well as a concluding stage of 10 min at 72° C. ("final extension"). The following sequences of oligonucleotides and primers are stated in the 5'-3' direction. PCR Primer Sequences:

```
BACT-TM.5:
                                    (SEQ ID NO:13)
TCA CCC ACA CTG TGC CCA TCT ACG A

BACT-TM.3:
                                    (SEQ ID NO:14)
CAG CGG AAC CGC TCA TTG CCA ATG G
```

Sequences of the "Feed" Oligonucleotides:

```
GAP P78 3'P:
                                    (SEQ ID NO:8)
GCG TCA AAG GTG GAG GAG TGG GTG TCG CTG TTG AAG

TCA TGA CTT CAA CAG CGA CAC CCA CTC CTC CAC CTT

TGA CGC [Phosp-Q]
([Phosp-Q]:3'-phosphate)

GAP P78 3'P-Thio:
                                    (SEQ ID NO:9)
GCG TCA AAG GTG GAG GAG TGG GTG TCG CTG TTG AAG

TCA TGA CTT CAA CAG CGA CAC CCA CTC CTC CAC CTT

TGA CT*C [Phosp-Q]
([Phosp-Q]:3'-phosphate; *:phosphothioate in the
backbone)

N14-degAATAAA:
                                    (SEQ ID NO:10)
NNN NNN NNN NNN NNH HND DVA ATA AA pA-I:
                                    (SEQ ID NO:11)
III III III III III III III AAT AAA
```

5 µl of each PCR reaction was analysed on an ethidium bromide stained agarose gel (2%). A 100 bp ladder (Invitrogen, 15628-050) served as a size standard. The FIGS. 4A to 4D show agarose gel analyses of the PCR products to investigate the effect of oligonucleotides with different properties (GAP P78 3'P, GAP P78 3'P-Thio, N14-degAATAAA, PA-I) on the PCR amplification of β-actin. M=marker.

The "feed" oligonucleotides already successfully tested for use with genomic DNA in the examples 2 and 3 were used in example 4 with a high fidelity PCR as template nucleic acid to amplify a 300 bp fragment from cDNA. In all cases a clear improvement in yield and sensitivity can be achieved. In comparison to PCR reactions without "feed" oligonucleotides, a successful PCR was possible by using considerably smaller quantities of template cDNA. The sensitivity could be increased up to 100-fold (experiment as per FIG. 4A), up to 10,000-fold (experiment as per FIG. 4B), up to 1,000-fold (experiment as per FIG. 4C) and up to 10,000-fold (experiment as per FIG. 4D). All oligonucleotides used in example 4 are therefore suitable as "feed" oligonucleotides for the increase in the yield and sensitivity of a high fidelity PCR.

EXAMPLE 5

In this example, the effect of single stranded 45 mer "feed" oligonucleotides which differ in the presence of a phosphothioate in the DNA backbone, on the PCR amplification of β-actin by means of high fidelity DNA polymerase was investigated.

The oligonucleotides GAP45-3'P and GAP45-Thio with the sequences stated below were added to the PCR. These are single stranded oligonucleotides which carry a 3'-phosphate instead of the 3'-OH group. Both varieties differ in the presence (GAP45-Thio) or the absence (GAP45-3'P) of a phosphothioate in the DNA backbone.

The design and procedure of the high fidelity PCR were as follows. ProofStart DNA polymerase (QIAGEN, catalogue number 202205) was used for the PCR reactions. Each reaction assay comprised 1× ProofStart PCR buffer, 1 U of ProofStart DNA polymerase, 1 µM each of β-actin forward and reverse primer and 0.3 mM each of dNTPs (dATP, dCTP, dGTP, dTTP) in a reaction volume of 20 µl. In duplicate assays 10 ng, 1 ng, 0.1 ng, 0.01 ng and 0.001 ng of K562 cDNA (from K562 cells, see general methods at the end of the examples) was added in each case and likewise a comparable quantity of water was added to another duplicate assay as a negative control (NTC: "no template control"). In addition, the oligonucleotides GAP45-3'P and GAP45-Thio were added in each case as "feed" within the meaning of the invention in a concentration of 0.3 µM, 1.0 µM, 3.0 µM and 10 µM. As a control, corresponding reactions were carried out in each case without "feed" oligonuceotides (caption in FIG. 5A: "control"). The samples were cooled during the preparation of the PCR.

The PCR protocol comprised an initial reactivation of the ProofStart DNA polymerase ("Hot Start") for 5 min at 95° C., followed by 35 cycles of 30 sec at 94° C., 60 sec at 61° C. and 1 min 30 sec at 72° C., as well as a concluding stage of 10 min at 72° C. ("final extension"). The following sequences of oligonucleotides and primers are stated in the 5'-3' direction.
PCR Primer Sequences:

```
BACT-TM.5:
                                          (SEQ ID NO:13)
TCA CCC ACA CTG TGC CCA TCT ACG A

BACT-TM.3:
                                          (SEQ ID NO:14)
CAG CGG AAC CGC TCA TTG CCA ATG G
```

Sequences of the "Feed" Oligonucleotides:

```
GAP45-3'P:
                                          (SEQ ID NO:5)
GCG TCA AAG GTG GAG GAG TGG GTG TCG CTG TTG AAG

TCA GAG GAG [Phosp-Q]
([Phosp-Q]:3'-phosphate)

GAP45-Thio:
                                          (SEQ ID NO:15)
GCG TCA AAG GTG GAG GAG TGG GTG TCG CTG TTG AAG TCA GAG GA*G [Phosp-Q]
([Phosp-Q]:3'-phosphate; *:phosphothioate in the
backbone)
```

As set forth above, GAP45-3'P has the same sequence as P45-GADPH.

Figure 5A:
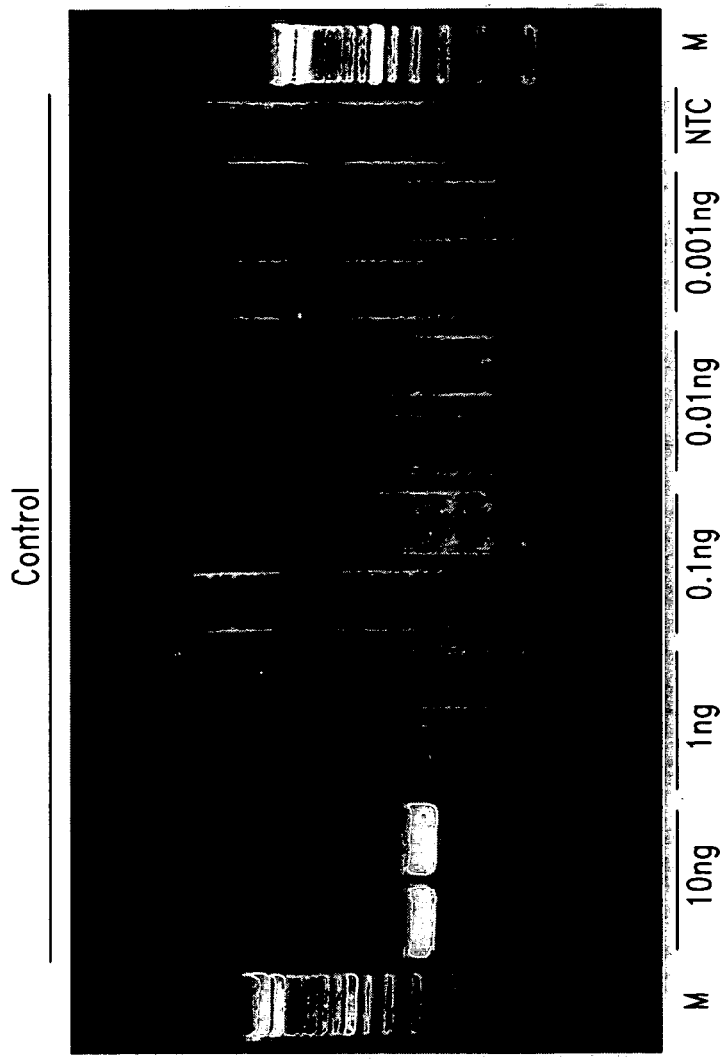
FIG. 5A to 5C agarose gel analyses of PCR products to investigate the effects of single stranded 45 mer "feed" oligonucleotides, which vary by the presence of a phosphothioate in the DNA backbone, on the PCR amplification of β-actin.
Figure 5B:
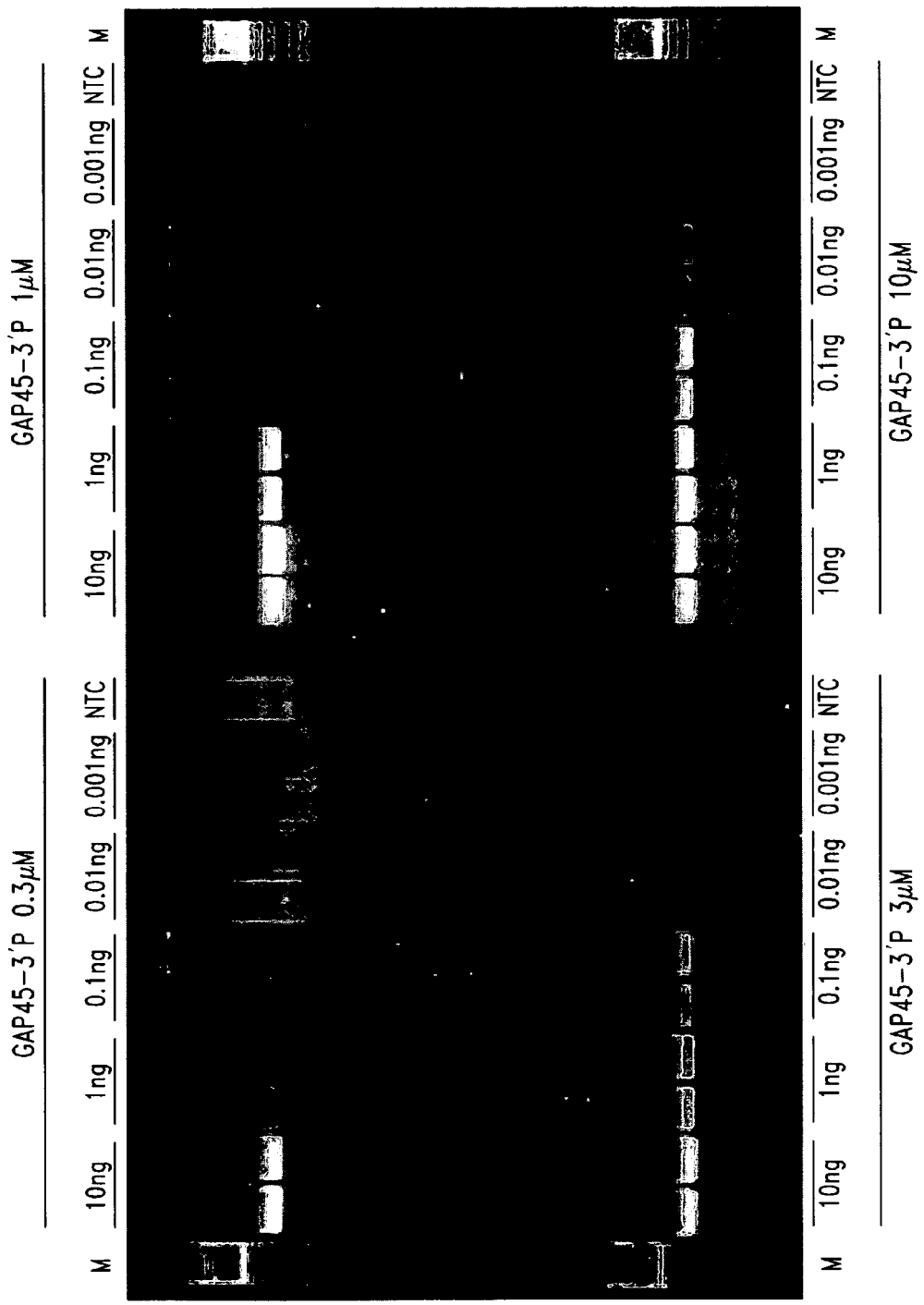
Figure 5C:
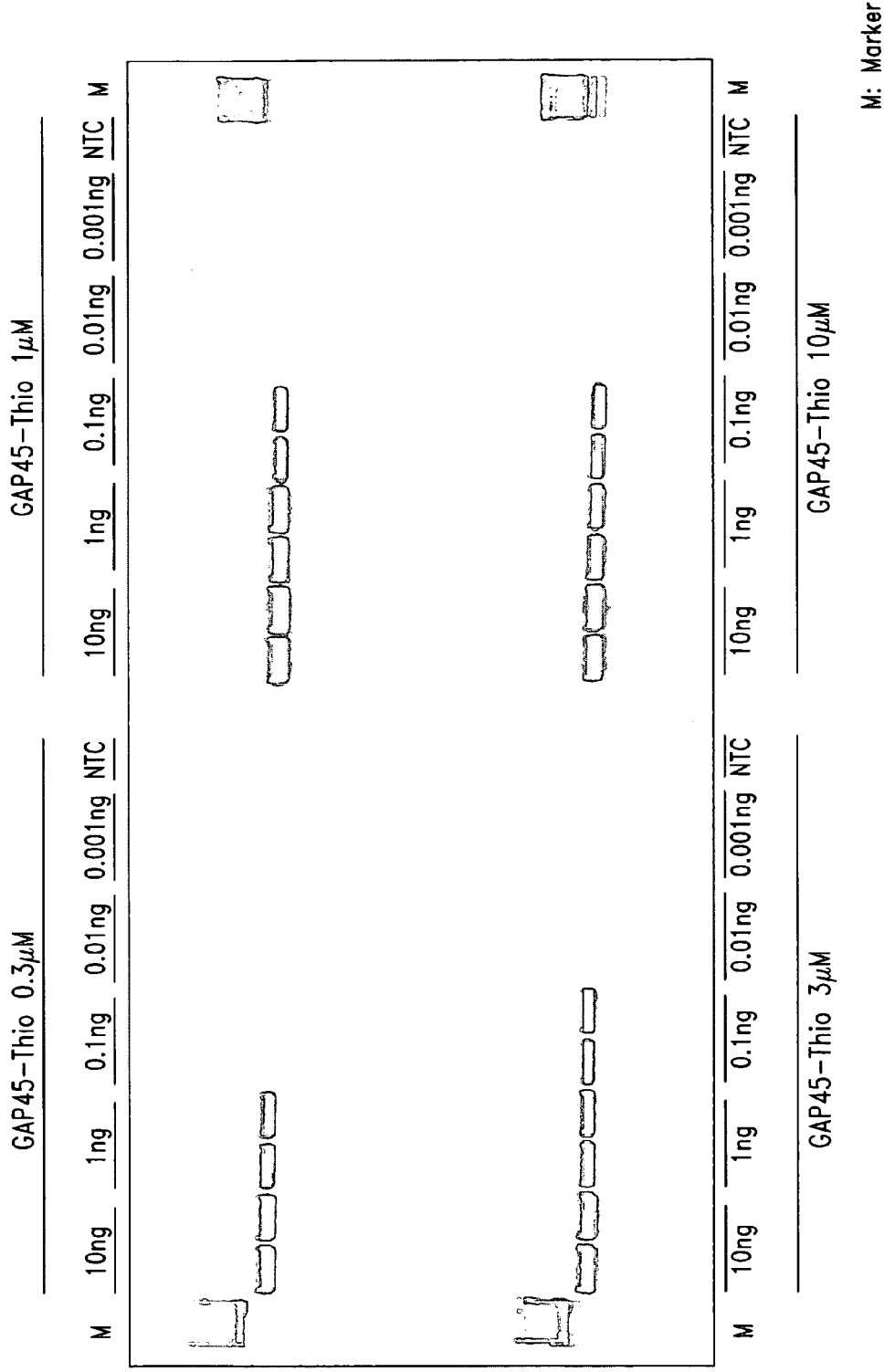

5 μl of each PCR reaction was analysed on an ethidium bromide stained agarose gel (2%). A 100 bp ladder (Invitrogen, 15628-050) served as a size standard. The FIGS. 5A to 5C show agarose gel analyses of the PCR products to investigate the effect of single stranded 45 mer "feed" oligonucleotides, which differ in the presence of a phosphotioate in the DNA backbone, on the PCR amplification of β-actin.

In all cases using both 45 mer "feed" oligonucleotides, a clear improvement in yield and sensitivity could be achieved. In comparison to PCR reactions without "feed" oligonucleotides, a successful PCR was possible by using considerably smaller quantities of template cDNA. The sensitivity in comparison to the control (FIG. 5A) could be increased up to 1,000-fold using GAP45-3'P (FIG. 5B) and up to 10,000-fold using GAP45-Thio. At the same time, the background often appearing as "smear" in the high fidelity PCR reactions was also clearly reduced.

EXAMPLE 6

In this example the effect of "feed" DNA oligonucleotides G45-TP-1sp-d and G45-TP-2sp-d, which comprise abasic spacers, on the high fidelity PCR by β-actin was investigated. The oligonucleotides G45-TP-1sp-d and G45-TP-2sp-d with the sequences stated below were added to the PCR. These are single stranded oligonucleotides, which carry a 3'-phosphate instead of the 3'-OH group as well as a phosphothioate instead of a phosphate between the last and penultimate 3'-base in the backbone of the DNA. Both variants differ in the presence of (G45-TP-1sp-d) and absence of (G45-TP-2sp-d) an abasic spacer.

The design and procedure of the high fidelity PCR were as follows. ProofStart DNA polymerase (QIAGEN, catalogue number 202205) was used for the PCR reactions. Each reaction assay comprised 1×ProofStart PCR buffer, 1 U of Proof-Start DNA polymerase, 1 μM each of β-actin forward and reverse primer and 0.3 mM each of dNTPs (dATP, dCTP, dGTP, dTTP) in a reaction volume of 20 μl. In the duplicate assays 10 ng, 1 ng, 0.1 ng, 0.01 ng and 0.001 ng of cDNA (from K562 cells, see general methods at the end of the examples) was added in each case and in a single assay a comparable quantity of water was added as a negative control (NTC: "no template control"). In addition, the oligonucleotides G45-TP-1sp-d and G45-TP-2sp-d were added each time as "feed" within the meaning of the invention, in a concentration of 0.3 μM, 1 μM, 3 μM and 10 μM. As a control, corresponding reactions were carried out in each case without "feed" oligonuceotides (caption in FIG. 5A: "control"). The samples were cooled during the preparation of the PCR.

The PCR protocol comprised an initial reactivation of the ProofStart DNA polymerase ("Hot Start") for 5 min at 95° C., followed by 35 cycles of 30 sec at 94° C., 60 sec at 61° C. and 1 min 30 sec at 72° C., as well as a concluding stage of 10 min at 72° C. ("final extension"). The following sequences of oligonucleotides and primers are stated in the 5'-3' direction.
PCR Primer Sequences:

```
BACT-TM.5:
                                          (SEQ ID NO: 13)
TCA CCC ACA CTG TGC CCA TCT ACG A

BACT-TM.3:
                                          (SEQ ID NO: 14)
CAG CGG AAC CGC TCA TTG CCA ATG G
```

Sequences of the "Feed" Oligonucleotides:

```
G45-TP-1sp-d:
                                          (SEQ ID NO: 16)
GCG TCA AAG GTG GAG GAG TGG GT [sp-d]GTC GCT GTT

GAA GTC AGA GGA *G[Phosp-Q]
([sp-d]: abasic spacers; [Phosp-Q]: 3'-phosphate;
*: phosphothioate in the backbone)

G45-TP-2sp-d:
                                          (SEQ ID NO: 17)
GCG TCA AAG GT[sp-d] GGA GGA GTG GGT [sp-d]GTC GCT

GTT GAA GTC AGA GGA *G[Phosp-Q]
([sp-d]: abasic spacers, [Phosp-Q]: 3'-Phosphate;
*: phosphothioate in the backbone)
```

Figure 6A:
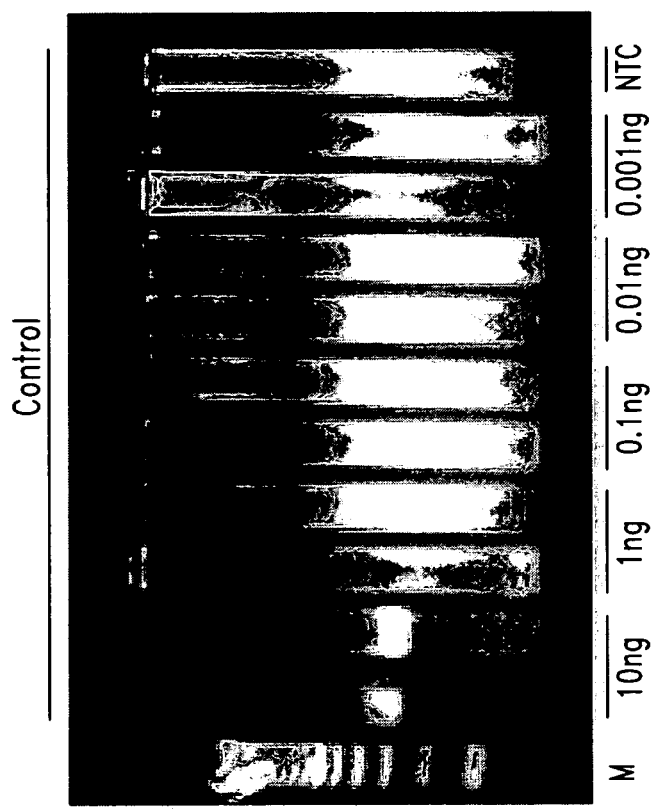
FIG. 6A to 6C agarose gel analyses to investigate the effects of "feed" oligonucleotides which comprise abasic spacers on the PCR amplification of β-actin.
Figure 6B:
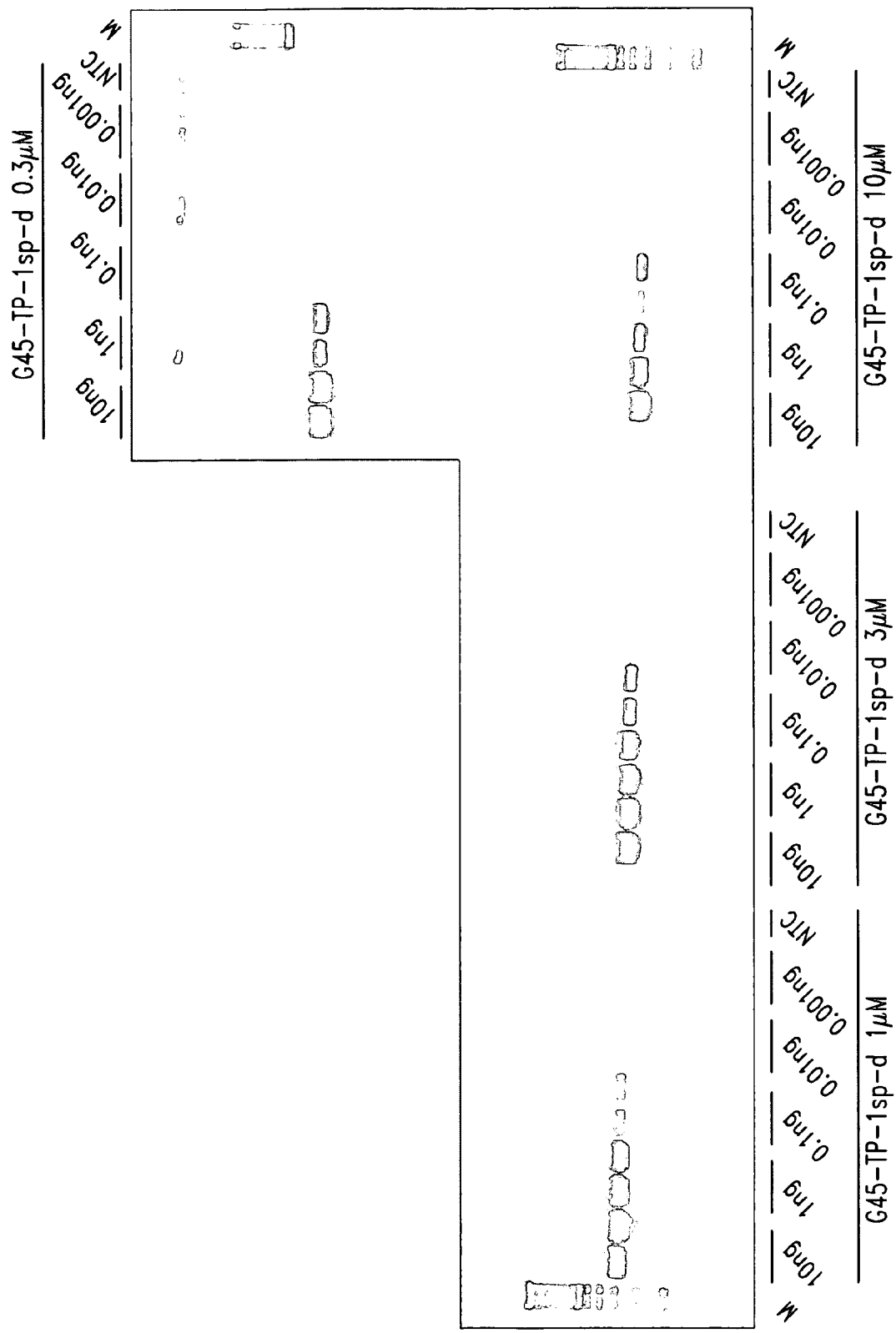
Figure 6C:
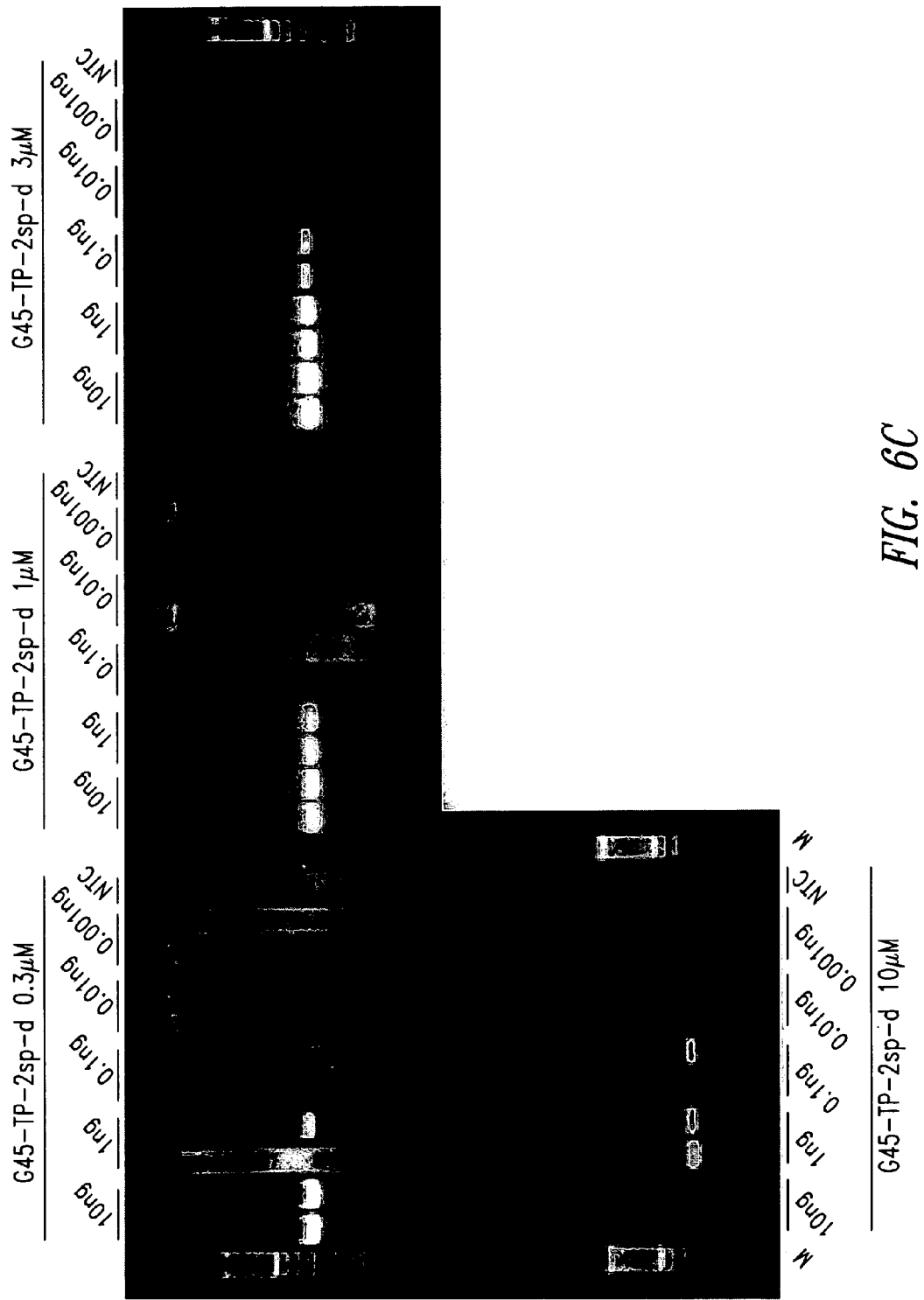

5 μl of each PCR reaction was analysed on an ethidium bromide stained agarose gel (2%). A 100 bp ladder (Invitrogen, 15628-050) served as a size standard. FIGS. 6A to 6C show agarose gel analyses of the PCR products to investigate the effect of "feed" oligonucleotides that contain abasic spacers, on the PCR amplification of β-Actin. M=marker.

In all cases using both 45 mer "feed" oligonucleotides with an abasic spacer (FIG. 6B) and two abasic spacers (FIG. 6C), a clear improvement in yield and sensitivity could be achieved. In comparison to PCR reactions without "feed" oligonucleotides (FIG. 6A), a successful PCR was possible by using considerably smaller quantities of template cDNA. The sensitivity in comparison to the control (FIG. 6A) could be increased up to 1,000-fold (experiment as per FIG. 6B) and also up to 10,000-fold in the experiment as per FIG. 6C. At the same time, the background often appearing as "smear" in the high fidelity PCR reactions was also clearly reduced.

EXAMPLE 7

In this example the effect of RNA used as "feed" within the meaning of the invention on the high fidelity PCR (PCR amplification of β-actin) was investigated. Commercially available transfer RNA (tRNA, R8508, Sigma GmbH, Taufkirchen bei Munich, Germany) as well as ribosomal RNA (rRNA, R6750, Sigma) was added as "feed" of the high fidelity PCR.

The design and procedure of the high fidelity PCR were as follows. ProofStart DNA polymerase (QIAGEN, catalogue number 202205) was used for the PCR reactions. Each reaction assay comprised 1× ProofStart PCR buffer, 1 U of Proof-Start DNA polymerase, 1 µM each of β-actin forward and reverse primer and 0.3 mM each of dNTPs (dATP, dCTP, dGTP, dTTP) in a reaction volume of 20 µl. In triplicate assays 100 ng, 10 ng, 1 ng, 0.1 ng and 0.01 ng of K562 cDNA (from K562 cells, see general methods) was added in each case and in a single assay a comparable quantity of water was added as a negative control (NTC: "no template control"). In addition, the "feed" within the meaning of the invention was added, in each case tRNA in a concentration of 4 ng, 40 ng, 400 ng and 4000 ng per 20 µl reaction assay, and rRNA in a concentration of 4 ng, 40 ng and 400 ng per 20 µl reaction assay. As a control, corresponding reactions were carried out in each case without "feed" RNA (caption in FIG. 7A: "control"). The samples were cooled during the preparation of the PCR.

The PCR protocol comprised an initial reactivation of the ProofStart DNA polymerase ("Hot Start") for 5 min at 95° C., followed by 35 cycles of 30 sec at 94° C., 60 sec at 61° C. and 1 min 30 sec at 72° C., as well as a concluding stage of 10 min at 72° C. ("final extension"). The following sequences of oligonucleotides and primers are stated in the 5'-3' direction. PCR Primer Sequences:

β-actin forward:
(SEQ ID NO: 13)
TCA CCC ACA CTG TGC CCA TCT ACG A

β-actin reverse:
(SEQ ID NO: 14)
CAG CGG AAC CGC TCA TTG CCA ATG G

Figure 7A:
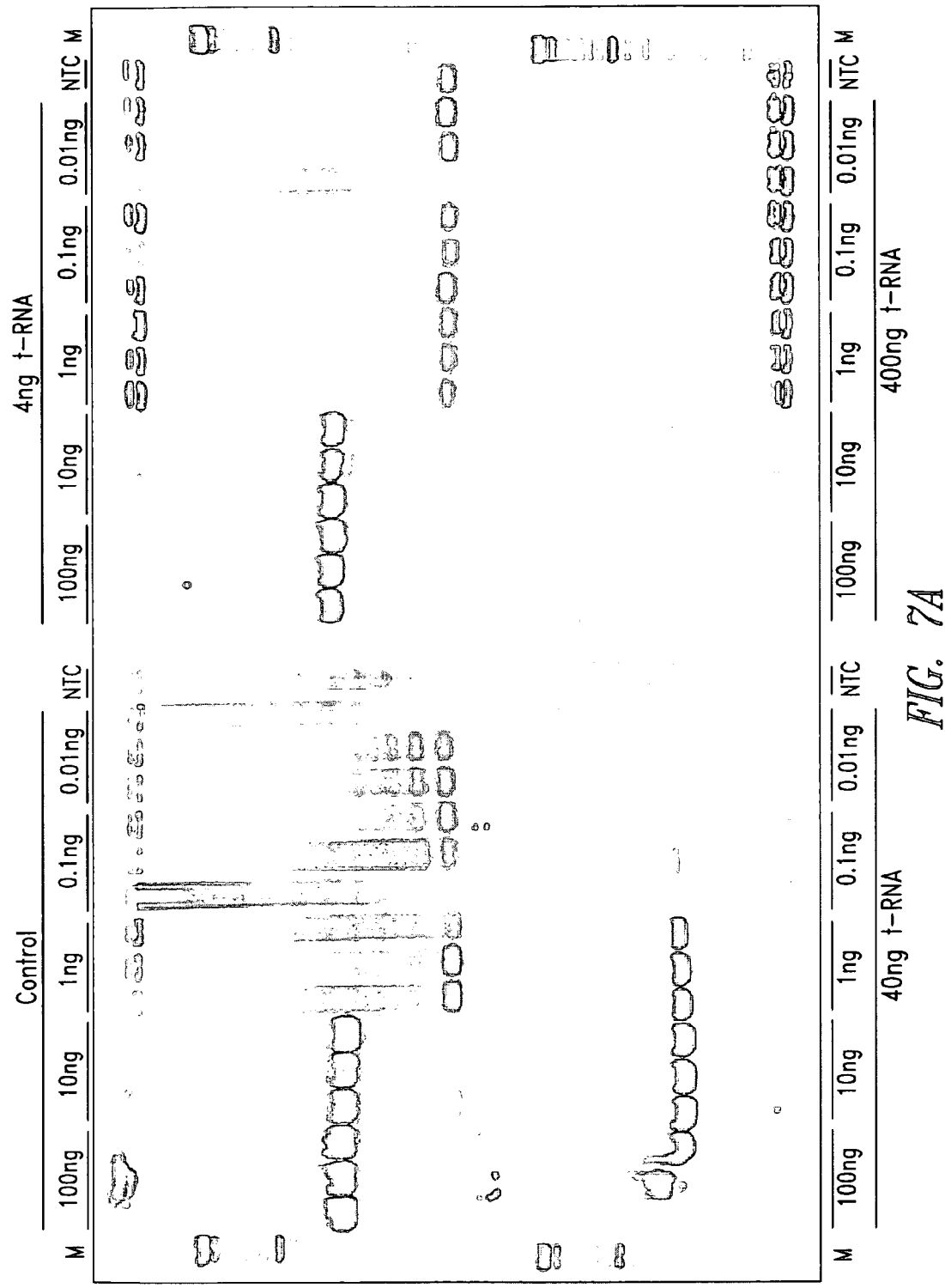
FIGS. 7A and 7B agarose gel analyses to investigate the effects of RNA as "feed" within the meaning of the invention on the PCR amplification of β-actin.
Figure 7B:
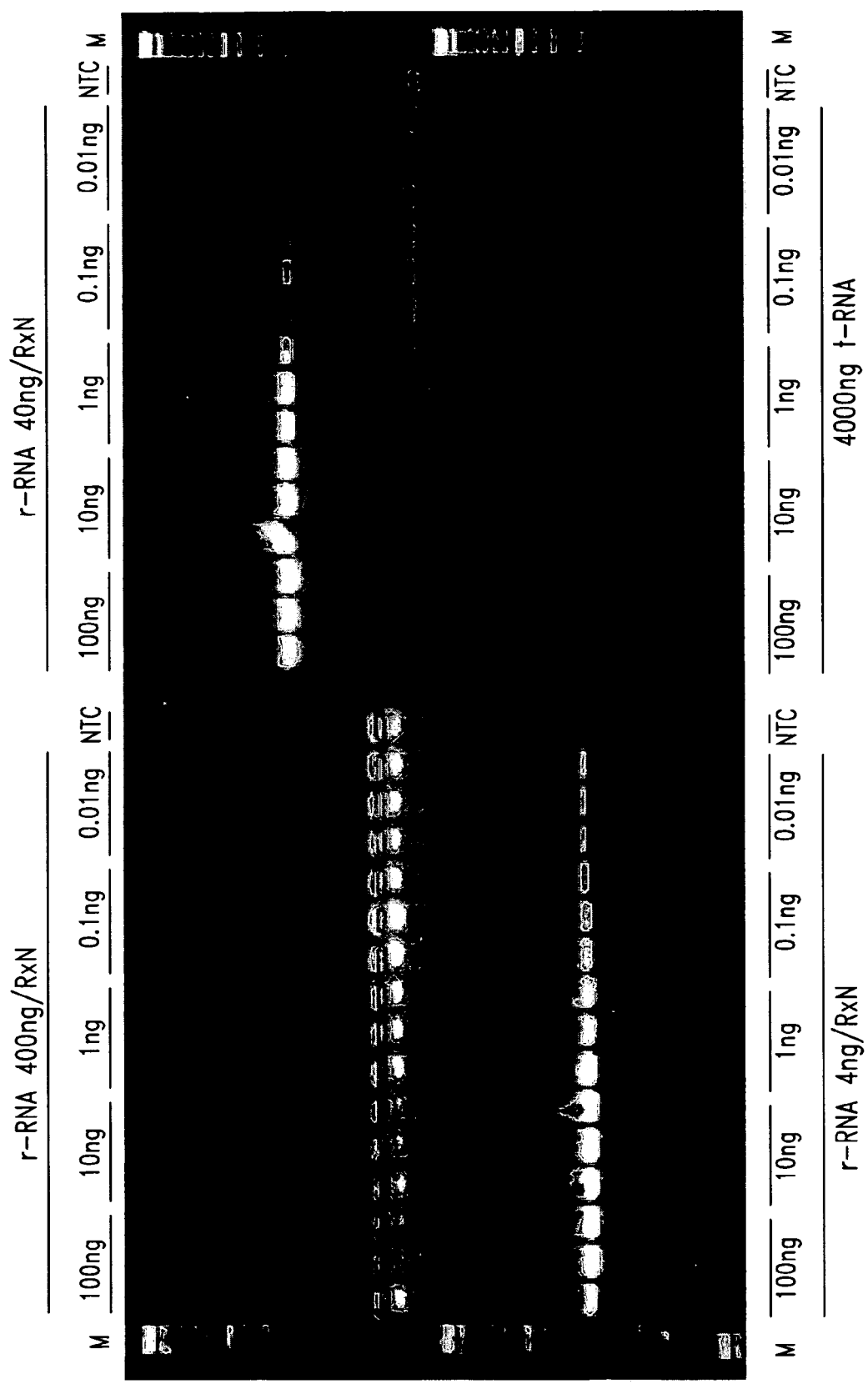

5 µl of each PCR reaction was analysed on an ethidium bromide stained agarose gel (2%). A 100 bp ladder (Invitrogen, 15628-050) served as a size standard. The FIGS. 7A and 7B show agarose gel analyses to investigate the effect of RNA as "feed" within the meaning of the invention on the PCR amplification of β-Actin. M=marker.

Surprisingly RNA as "feed" within the meaning of the invention is suitable to improve yield and sensitivity of the high fidelity PCR. Use of tRNA (FIG. 7A) could improve the sensitivity up to 100-fold. Use of rRNA (FIG. 7B) could even improve the sensitivity up to 1,000-fold. At the same time, with addition of RNA (FIGS. 7A and B) the background often appearing as "smear" in the high fidelity PCR was also clearly reduced.

EXAMPLE 8

In this example the effect of RNA as "feed" within the meaning of the invention on the high fidelity PCR (the PCR amplification of β-actin) was investigated. Commercially available poly-A-RNA (QIAGEN, 1010373) was added as "feed" of the high fidelity PCR. This is a homo-A-polmer, which comprises of a heterogeneous mixture of different length poly(A) molecules (main fraction between 0.2 kb and 5.0 kb).

The design and procedure of the high fidelity PCR were as follows. ProofStart DNA polymerase (QIAGEN, catalogue number 202205) was used for the PCR reactions. Each reaction assay comprised 1× ProofStart PCR buffer, 2.5 U of ProofStart DNA polymerase, 1 µM each of β-actin forward and reverse primer and 0.3 mM each of dNTPs (dATP, dCTP, dGTP, dTTP) in a reaction volume of 50 µl. In triplicate assays 100 ng, 10 ng, 1 ng, 0.1 ng and 0.01 ng of cDNA (from K562 cells, see general methods at the end of the examples) was added per reaction and in a single assay a comparable quantity of water was added as a negative control (NTC: "no template control"). In addition, the poly-A-RNA as "feed" within the meaning of the invention was added, in each case in a concentration of 20 ng, 200 ng, 2000 ng and 20,000 ng per 50 µl reaction assay. As a control, corresponding reactions were carried out in each case without "feed" RNA (caption in FIG. 8A: "control"). The samples were cooled during the preparation of the PCR.

The PCR protocol comprised an initial reactivation of the ProofStart DNA polymerase ("Hot Start") for 5 min at 95° C., followed by 40 cycles of 30 sec at 94° C., 60 sec at 61° C. and 1 min 30 sec at 72° C., as well as a concluding stage of 10 min at 72° C. ("final extension"). The following sequences of oligonucleotides and primers are stated in the 5'-3' direction. PCR Primer Sequences:

β-actin forward:
(SEQ ID NO: 13)
TCA CCC ACA CTG TGC CCA TCT ACG A

β-actin reverse:
(SEQ ID NO: 14)
CAG CGG AAC CGC TCA TTG CCA ATG G

Figure 8A:
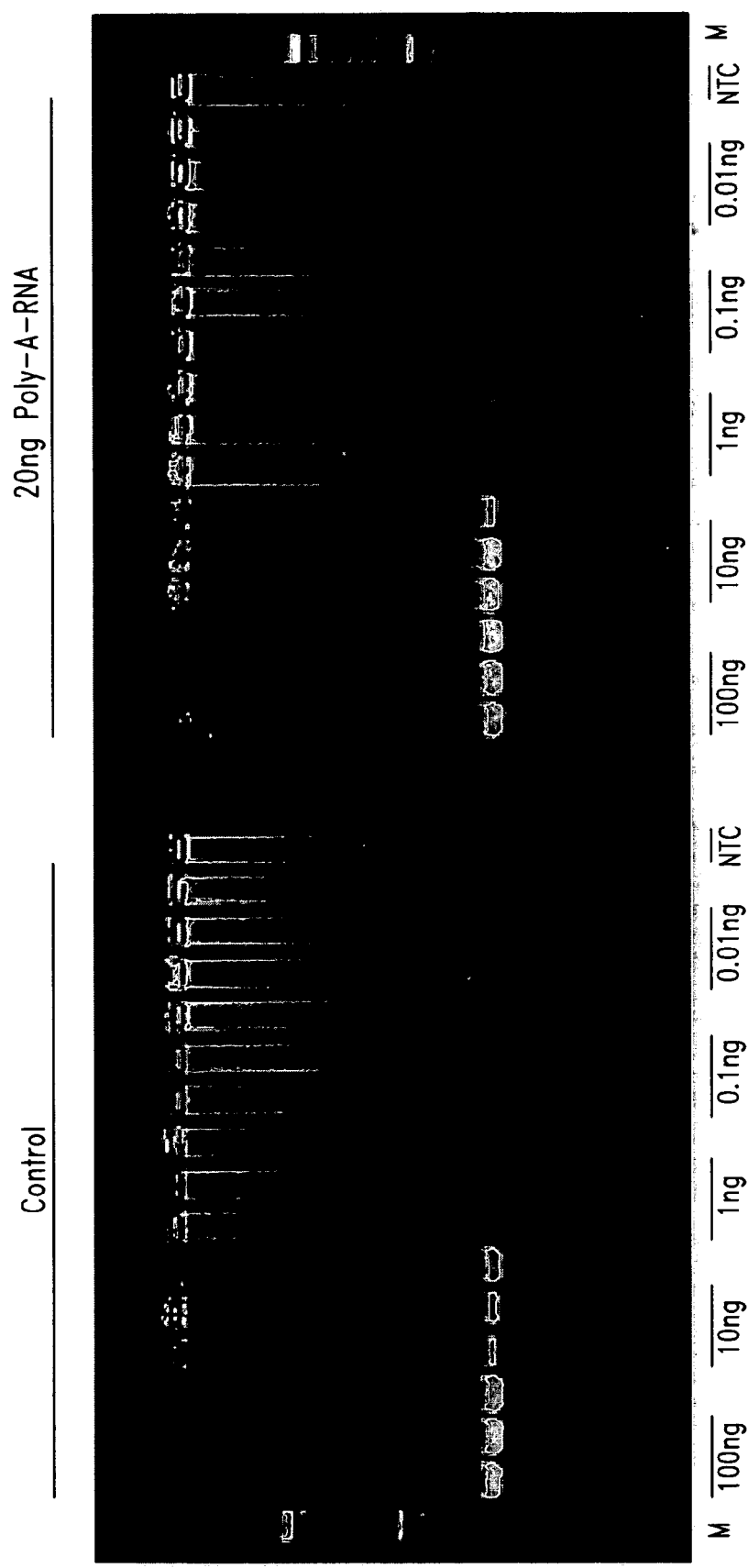
FIGS. 8A and 8B agarose gel analyses to investigate the effects of the addition of poly-A RNA on the PCR amplification of β-actin.
Figure 8B:
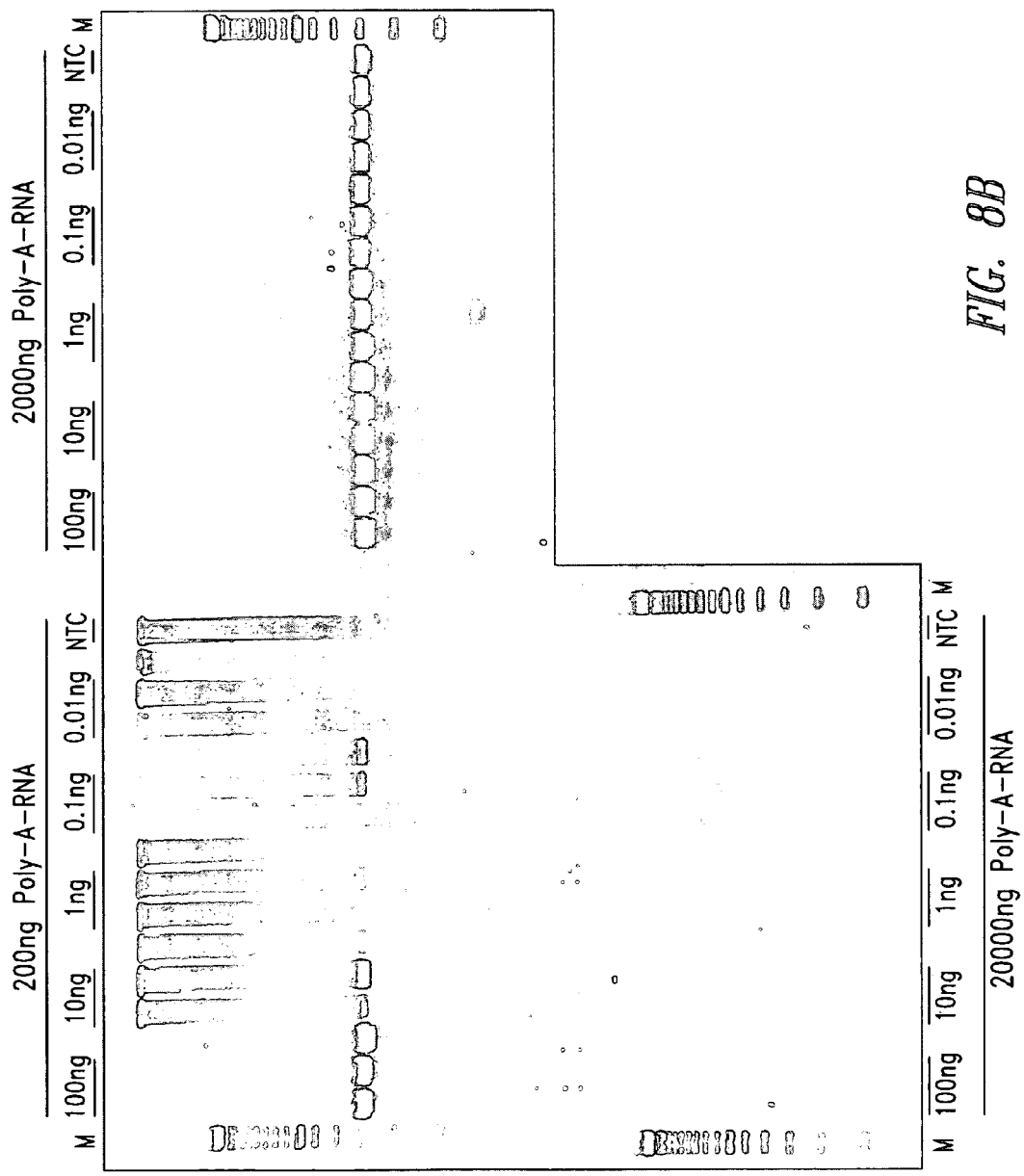

10 µl of each PCR reaction was analysed on an ethidium bromide stained agarose gel (1%). A 100 bp ladder (Invitrogen, 15628-050) served as a size standard. The FIGS. 8A and 8B show agarose gel analyses to investigate the effect of the added poly-A-RNA on the PCR amplification of β-actin.

Surprisingly poly-A-RNA used as "feed" within the meaning of the invention is also suitable to improve yield and sensitivity of the high fidelity PCR. Use of poly-A-RNA could improve the sensitivity up to 10,000-fold. At the same time, with addition of RNA (compare FIGS. 8A and B) the background often appearing as "smear" in the high fidelity PCR reactions was also clearly reduced.

EXAMPLE 9

In this example, the effect of PCR primers which carry a phosphothioate between the last and 3'-base in the sugar-phosphate backbone of the DNA on the high fidelity PCR (the amplification of β-Actin) was to be investigated and compared to standard PCR primers. In the literature (Skerra, A., *Phosphoro phosphothioat primers improve the amplification of DNA sequences by DNA polymerases with proofreading activity*, Nucleic Acids Res, 1992, 20(14), 3551-3554), a positive effect is described for PCR primers that carry a phosphothioate between the last and penultimate 3'-base in the sugar-phosphate backbone. In this experiment, the effect of such primers on the amplification of the β-actin PCR system used in Example 4 to 8 was to be investigated in comparison to standard primers. The effect of the primers was tested in a concentration range of 0.2 µM to 1 µM.

The design and procedure of the high fidelity PCR were as follows. ProofStart DNA polymerase (QIAGEN, catalogue number 202205) was used for the PCR reactions. Each reaction assay comprised 1× ProofStart PCR buffer, 2.5 U of ProofStart DNA polymerase, 0.2 µM, 0.5 µM or 1 µM each of β-actin forward-Thio and reverse-Thio primer and 0.3 mM each of dNTPs (dATP, dCTP, dGTP, dTTP) in a reaction volume of 50 μl. In duplicate assays 100 ng, 10 ng, 1 ng, of K562 cDNA was added in each case and likewise in duplicate assays a comparable quantity of water was added as a negative control (NTC: "no template control"). As a control, corresponding PCR reactions were carried out each with 0.2 μM, 0.5 μM or 1 μM of both standard primers (β-actin forward and reverse) in each case (caption: "standard primers"). The samples were cooled during the preparation of the PCR.

The PCR protocol comprised an initial reactivation of the ProofStart DNA polymerase ("Hot Start") for 5 min at 95° C., followed by 35 cycles of 30 sec at 94° C., 60 sec at 61° C. and 1 min 30 sec at 72° C., as well as a concluding stage of 10 min at 72° C. ("final extension"). The following sequences of primers are stated in the 5'-3' direction.

PCR Primer Sequences:

β-actin forward:
(SEQ ID NO: 13)
TCA CCC ACA CTG TGC CCA TCT ACG A

β-actin reverse:
(SEQ ID NO: 14)
CAG CGG AAC CGC TCA TTG CCA ATG G

β-actin forward-Thio:
(SEQ ID NO: 18)
TCA CCC ACA CTG TGC CCA TCT ACG *A

β-actin reverse-Thio:
(SEQ ID NO: 19)
CAG CGG AAC CGC TCA TTG CCA ATG *G
(*: phosphothioate in the backbone)

Figure 9:
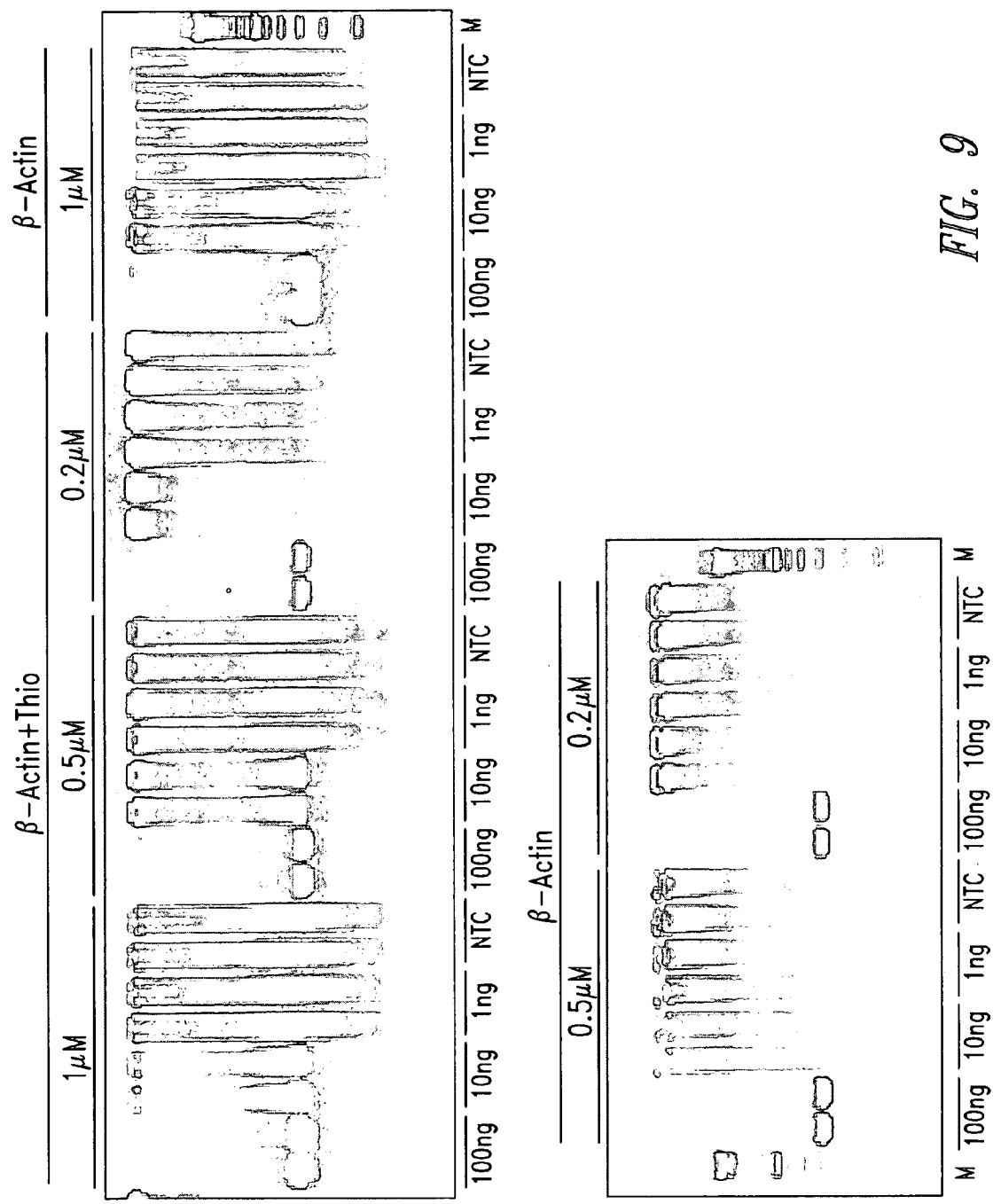
FIG. 9 an agarose gel analysis to investigate the effects of PCR primers which carry a phosphotioate between the last and penultimate 3'-bases in the sugar-phosphate backbone of the DNA on the PCR amplification of β-actin in comparison to standard PCR primers.

10 μl of each PCR reaction was analysed on an ethidium bromide stained agarose gel (2%). A 100 bp ladder (Invitrogen, 15628-050) served as a size standard. FIG. 9 shows an Agarose Gel Analysis to investigate the effect of the PCR primers which carry a phosphothioate between the last and penultimate 3' base in the sugar-phosphate backbone of the DNA on the PCR amplification of β-actin in comparison with standard PCR primers. M=marker.

Using PCR primers that carry a phosphothioate between the last and penultimate 3' base in the sugar-phosphate backbone, it was possible achieve a small improvement in yield and sensitivity in comparison to standard primers. The increase in sensitivity was 10-fold maximum. In contrast, sensitivity in the same PCR system in Examples 4 to 8 was increased up to 10,000-fold.

At the same time, use of PCR primers, which carry a phosphothioate between the last and penultimate 3' base in the sugar-phosphate backbone of the DNA, showed no reduction on the background often appearing as "smear" in the high fidelity PCR reactions. In comparison to the state of the art, the use of "feed" within the meaning of the invention demonstrated a significant improvement of the high fidelity PCR.

EXAMPLE 10

This example concerns the effect of hairpin "feed" oligonucleotides on the PCR amplification of a 2 kb fragment from the murine PKC gene locus using the enzyme VentR. In particular, the effect of the hairpin "feed" DNA oligonucleotide GAP P78 3'P-Thio on the high fidelity PCR using a high fidelity DNA polymerase from several archaeabacteria genera was investigated in this example. The enzyme VentR (New England Biolabs, M0254S) originally comes from *Thermococcus* spec. whilst the ProofStart polymerase used in the previous examples was originally isolated from *Pyrococcus* spec. In addition, in comparison to the ProofStart polymerase, VentR also lacks a PCR Hot-Start. The oligonucleotide GAP P78 3'P-Thio was already described in detail in Example 2.

The design and procedure of the high fidelity PCR were as follows. VentR polymerase (New England Biolabs, catalogue number M0254S) was used for the PCR reactions. Each reaction assay comprised 1× ThermoPol Reaction PCR buffer, 2.5 U of VentR DNA polymerase, 0.4 μM each of MPUC forward and reverse primer and 0.4 mM each of dNTPs (dATP, dCTP, dGTP, dTTP) in a reaction volume of 50 μl. In triplicate assays 100 ng, 25 ng, 2.5 ng, and 0.25 ng of 3T3 DNA was added in each case as well as a comparable quantity of water as a negative control (NTC: "no template control"). As a control, corresponding PCR reactions were carried out without "feed" oligonucleotide (caption in FIG. 10: "control"). The samples were cooled during the preparation of the PCR.

The PCR protocol comprised of 40 cycles of 30 sec at 94° C., 60 sec at 61° C. and 1 min 30 sec at 72° C. as well as a concluding stage of 10 min at 72° C. ("final extension"). The following sequences of oligonucleotides and primers are stated in the 5'-3' direction.

PCR Primer Sequences:

MPUC 3:
(SEQ ID NO: 20)
GCT GCT TGA AGA AAC GAG CGG TG

MPUG5 + 258:
(SEQ ID NO: 21)
CTG CAC CTT CTG GAA TTC CGA CTC

Sequences of the "Feed" Oligonucleotides:

GAP P78 3'P-Thio:
(SEQ ID NO:9)
GCG TCA AAG GTG GAG GAG TGG GTG TCG CTG TTG AAG

TCA TGA CTT CAA CAG CGA CAC CCA CTC CTC CAC CTT

TGA CG*C [Phosp-Q]
([Phosp-Q]: 3'-phosphate; *: phosphothioate in the backbone)

Figure 10:
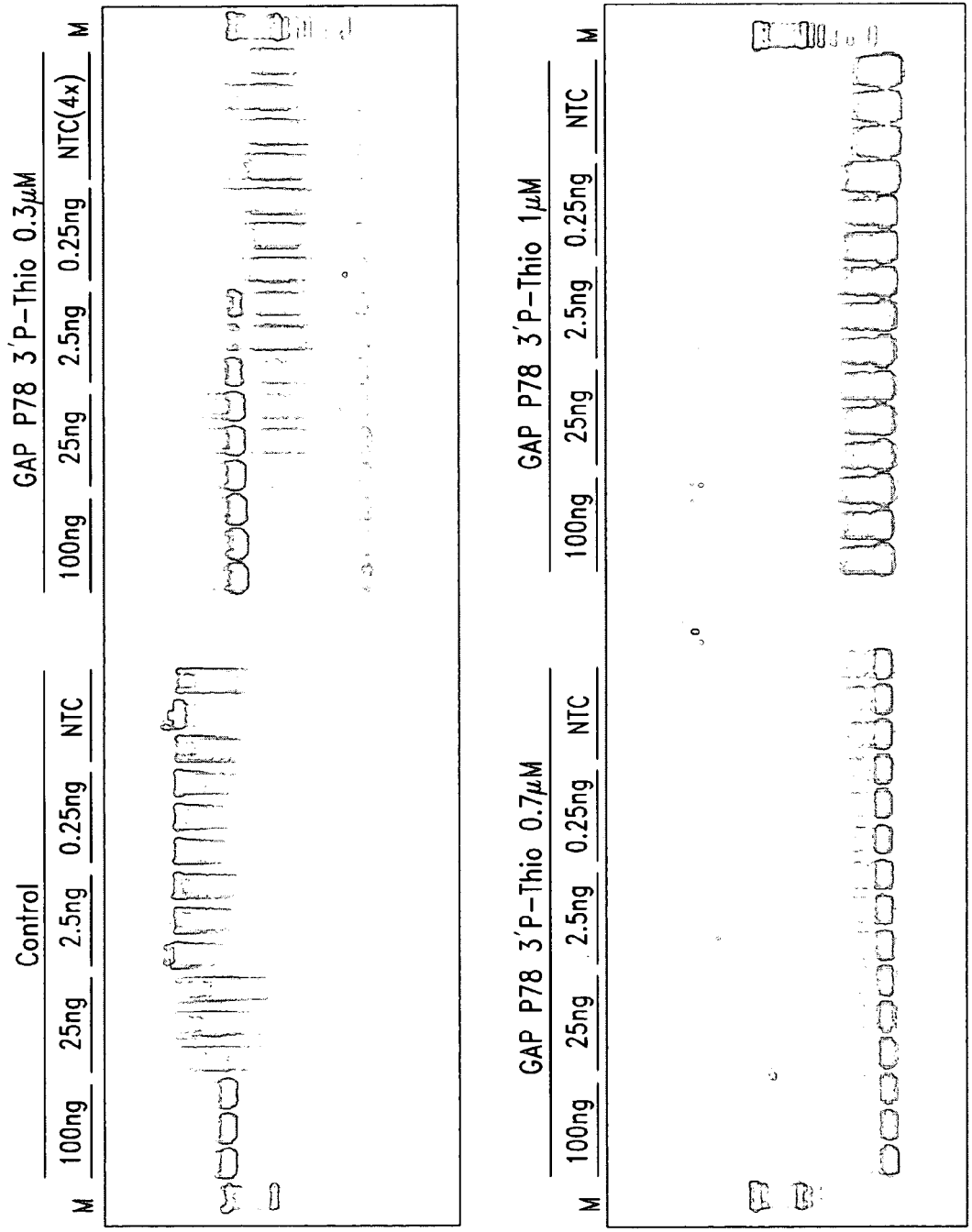
FIG. 10 an agarose gel analysis to investigate the effects of hairpin "feed" oligonucleotides on the PCR amplification of a 2 kb fragment from the murine PKC gene pool using the VentR enzyme.

10 μl of each PCR reaction was analysed on an ethidium bromide stained agarose gel (2%). A 100 bp ladder (Invitrogen, 15628-050) served as a size standard. FIG. 10 shows an agarose gel analysis to investigate the effect of the hairpin "feed" oligonucleotides on the PCR amplification of a 2 kb fragment from the murine PKC gene locus using the VentR enzyme. M=marker.

The use of the "feed" within the meaning of the invention is also compatible with a high fidelity DNA polymerase from another archaea genus and allows an improvement in yield and sensitivity of the high fidelity PCR. Here, the addition of the hairpin "feed" oligonucleotide GAP P78 3'P-Thio leads to an improvement in sensitivity for a 2 kb PCR product of up to 40-fold.

EXAMPLE 11

In this example the effect of the "feed" DNA oligonucleotide N40-thio on the high fidelity PCR (PCR amplification of β-actin) using a high fidelity DNA polymerase from several archaeabacteria genera was tested. The polymerase VentR (New England Biolabs, M0254S) originally comes from *Thermococcus* spec. whilst the ProofStart polymerase was originally isolated from *Pyrococcus* spec. In addition, in comparison to the ProofStart polymerase, VentR also lacks a PCR Hot-Start. The "feed" oligonucleotide is a single stranded oligonucleotide with a random sequence of A, C, G and T (N), which carries a 3'-phosphate instead of the 3'-OH group and also comprises a phosphothioate between the last and penultimate 3'-base in the sugar-phosphate backbone of the DNA.

The design and procedure of the high fidelity PCR were as follows. VentR polymerase (New England Biolabs, catalogue number M0254S) was used for the PCR reactions. Each reaction assay comprised 1× ThermoPol Reaction PCR buffer, 1.25 U of VentR DNA polymerase, 0.4 µM each of β-actin forward and reverse primer and 0.4 mM each of dNTPs (dATP, dCTP, dGTP, dTTP) in a reaction volume of 25 µl. In triplicate assays 100 ng, 10 ng, 1 ng, 0.1 ng and 0.01 ng of K562 DNA was added in each case as well as a comparable quantity of water as a negative control (NTC: "no template control"). In addition, the "feed" oligonucleotide N40-thio within the meaning of the invention was added in each case in a concentration of 0.3 µM, 0.7 µM or 1 µM. As a control, corresponding PCR reactions were carried out without "feed" oligonucleotide (caption in FIG. 11: "control"). The samples were cooled during the preparation of the PCR.

The PCR protocol comprised of 40 cycles of 30 sec at 94° C., 60 sec at 61° C. and 1 min 30 sec at 72° C. as well as a concluding stage of 10 min at 72° C. ("final extension"). The following sequences of oligonucleotides and primers are stated in the 5'-3' direction.

PCR Primer Sequences:

β-actin forward:
(SEQ ID NO: 13)
TCA CCC ACA CTG TGC CCA TCT ACG A

β-actin reverse:
(SEQ ID NO: 14)
CAG CGG AAC CGC TCA TTG CCA ATG G

Sequences of the "Feed" Oligonucleotides:

N40-Thio:
(SEQ ID NO: 22)
NNN NNN NNN NNN NNN NNN NNN NNN NNN NNN NNN NNN
NN*N [Phosp-Q]
(N: A, C, G, T; [Phosp-Q]: 3'-phosphate;
*: phosphothioate in the backbone)

Figure 11:
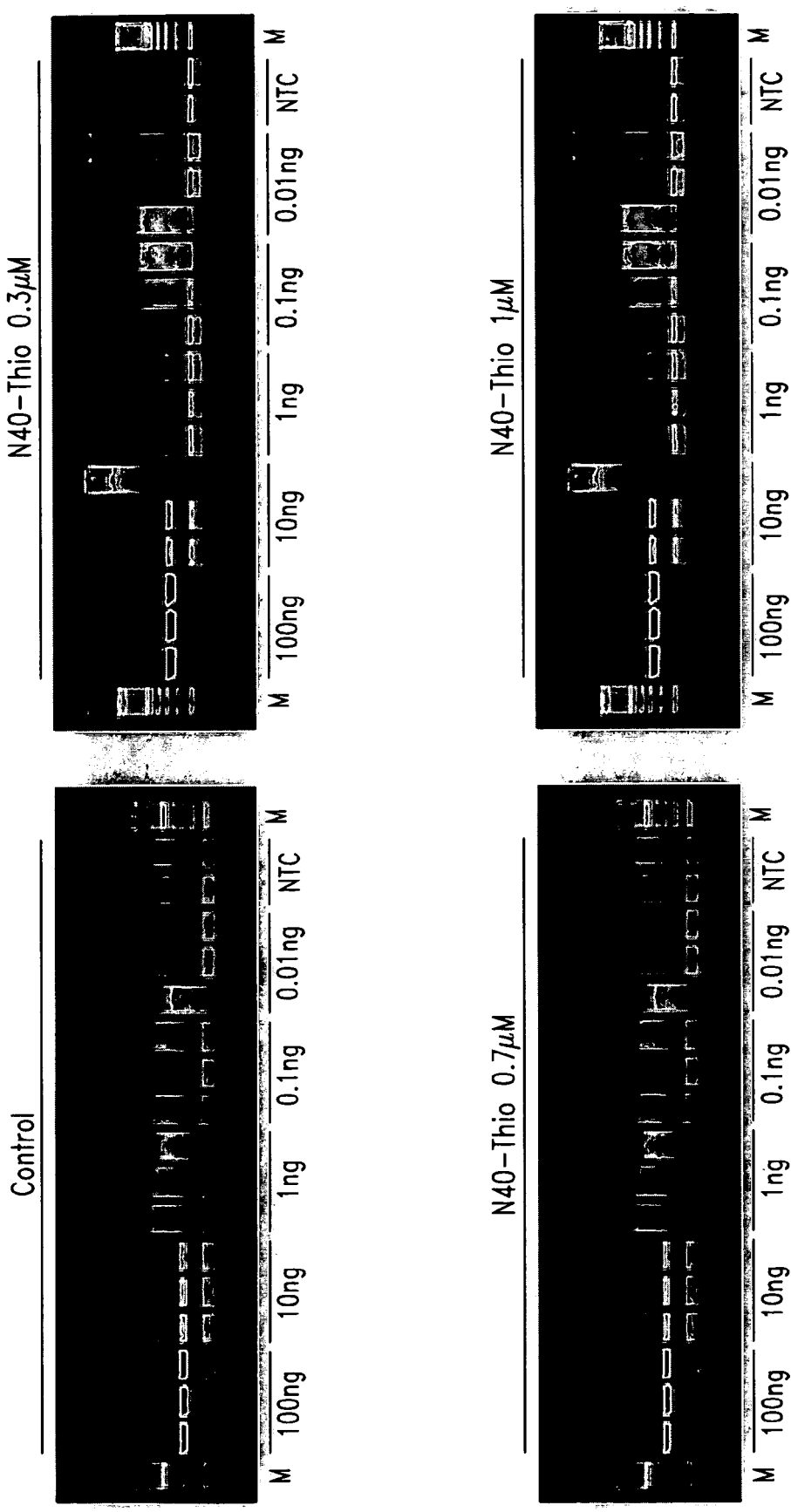
FIG. 11 an agarose gel analysis to investigate the effects of "feed" oligonucleotides on the PCR amplification of β-Actin using the VentR enzyme.

10 µl of each PCR reaction was analysed on an ethidium bromide stained agarose gel (1%). A 100 bp ladder (Invitrogen, 15628-050) served as a size standard. FIG. 11 shows an agarose gel analysis to investigate the effect of "feed" oligonucleotides on the PCR amplification of β-actin using the VentR enzyme. M=marker.

The addition of the "feed" oligonucleotide N40-thio leads here to an improvement in yield as well as an improvement in sensitivity by a factor of 10. Thus it is a suitable "feed" oligonucleotide within the meaning of this invention.

EXAMPLE 12

In this example, the effect of the "feed" DNA oligonucleotide GAP45-thio on the high fidelity PCR (PCR amplification of a 2 kb fragment from the murine PKC gene locus) using a high fidelity DNA polymerase from several genera of archaea bacteria was investigated. The enzyme VentR used (New England Biolabs, M0254S) originally came from *Thermococcus* spec. whilst the ProofStart polymerase was originally isolated from *Pyrococcus* spec. The oligonucleotide GAP45-Thio has already been described in detail in Example 5.

The design and procedure of the high fidelity PCR were as follows. VentR polymerase (New England Biolabs, catalogue number M0254S) was used for the PCR reactions. Each reaction assay comprised 1× ThermoPol Reaction PCR buffer, 1.25 U of VentR DNA polymerase, 0.4 µM each of MPUC forward and reverse primer and 0.4 mM each of dNTPs (dATP, dCTP, dGTP, dTTP) in a reaction volume of 25 µl. In triplicate assays 100 ng, 25 ng, 2.5 ng, and 0.25 ng of R×N were added in each case and in duplicate assays a comparable quantity of water was added as a negative control (NTC: "no template control"). In addition, the GAP45-Thio was added as "feed" oligonucleotide within the meaning of the invention in a concentration of 0.3 µM, 0.7 µM or 1 µM. As a control, corresponding reactions were carried out without "feed" oligonucleotide (caption in FIG. 12: "control"). The samples were cooled during the preparation of the PCR.

The PCR protocol comprised of 40 cycles of 30 sec at 94° C., 60 sec at 61° C. and 1 min 30 sec at 72° C. as well as a concluding stage of 10 min at 72° C. ("final extension"). The following sequences of oligonucleotides and primers are stated in the 5'-3' direction.

PCR Primer Sequences:

MPUC 3:
(SEQ ID NO: 20)
GCT GCT TGA AGA AAC GAG CGG TG

MPUC5 + 258:
(SEQ ID NO: 21)
CTG CAC CTT CTG GAA TTC CGA CTC

Sequences of the "Feed" Oligonucleotides:

GAP45-Thio:
(SEQ ID NO: 15)
GCG TCA AAG GTG GAG GAG TGG GTG TCG CTG TTG AAG
TCA GAG GA*G [Phosp-Q]
([Phosp-Q]: 3'-phosphate; *: phosphothioate in the backbone)

Figure 12:
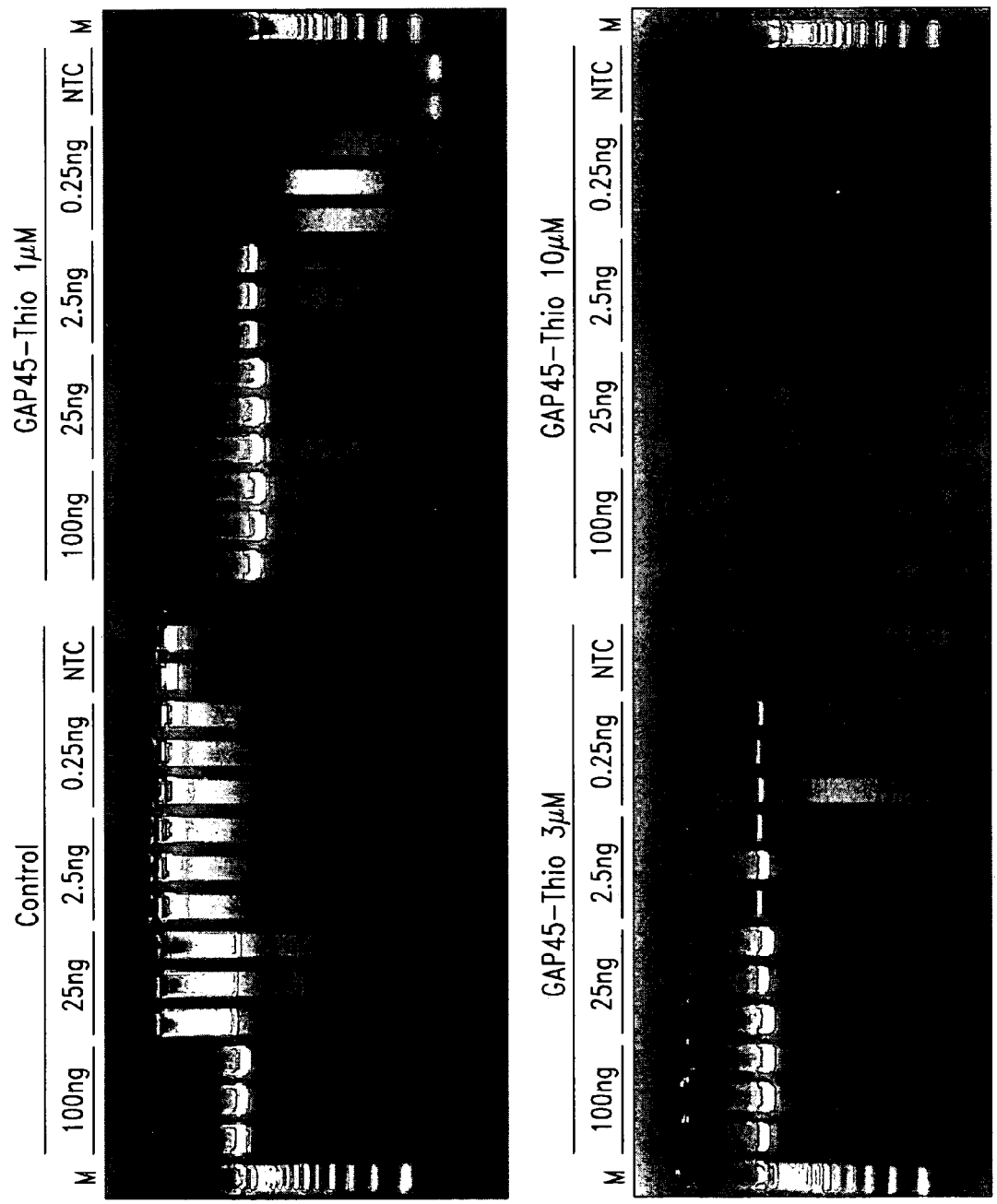
FIG. 12 an agarose gel analysis to investigate the effects of "feed" oligonucleotides on the PCR amplification of a 2 kb fragment from the murine PKC gene locus using the VentR enzyme.

10 µl of each PCR reaction was analysed on an ethidium bromide stained agarose gel (2%). A 100 bp ladder (Invitrogen, 15628-050) served as a size standard. FIG. 12 shows the effect of "feed" oligonucleotides on the PCR amplification of a 2 kb fragment from the murine PKC gene pool using the VentR enzyme. M=marker.

The use of the "feed" oligonucleotide GAP45-Thio could improve the sensitivity up to 400-fold. At the same time, the background often appearing as "smear" in the high fidelity PCR reactions was also clearly reduced.

EXAMPLE 13

In this example, the effect of the "feed" oligonucleotide N40-Thio, in conjunction with variable concentrations of PCR primers, on the amplification of β-actin was investigated. In particular, the effect of the "feed" DNA oligonucleotide N40-Thio on the high fidelity PCR was investigated in the presence of variable concentrations of PCR primers and compared with reactions without "feed" oligonucleotide in this example. The "feed" oligonucleotide N40-Thio used has already been described in detail in Example 11. The effect of the primer concentration was tested in a concentration range of 0.2 µM to 1 µM.

The design and procedure of the high fidelity PCR were as follows. ProofStart DNA polymerase (QIAGEN, catalogue number 202205) was used for the PCR reactions. Each reaction assay comprised 1× ProofStart PCR buffer, 1.25 U of ProofStart DNA polymerase, 0.2, 0.5 and 1 µM each of β-actin forward and reverse primer and 0.3 mM each of dNTPs (dATP, dCTP, dGTP, dTTP) in a reaction volume of 25 µl. In duplicate assays 1 ng, 0.1 ng and 0.01 ng, of K562 cDNA (from K562 cells, see general methods at the end of the examples) was added per reaction in each case and in a single assay a comparable quantity of water was added as a negative control (NTC: "no template control"). In addition, the N40-Thio was added as "feed" oligonucleotide within the meaning of the invention in a concentration of 1 µM. As a control, corresponding reactions were carried out without "feed" oligonucleotide (caption in FIG. 13: "control"). The samples were cooled during the preparation of the PCR.

The PCR protocol comprised an initial reactivation of the ProofStart DNA polymerase ("Hot Start") for 5 min at 95° C., followed by 40 cycles of 30 sec at 94° C., 60 sec at 61° C. and 1 min 30 sec at 72° C., as well as a concluding stage of 10 min at 72° C. ("final extension"). The following sequences of oligonucleotides and primers are stated in the 5'-3' direction.

PCR Primer Sequences:

β-actin forward:
(SEQ ID NO: 13)
TCA CCC ACA CTG TGC CCA TCT ACG A

β-actin reverse:
(SEQ ID NO: 14)
CAG CAG CGG AAC CGC TCA TTG CCA ATG G

Sequences of the "Feed" Oligonucleotides:

N40-thio:
(SEQ ID NO: 22)
NNN NNN NNN NNN NNN NNN NNN NNN NNN NNN NNN NNN

Figure 13:
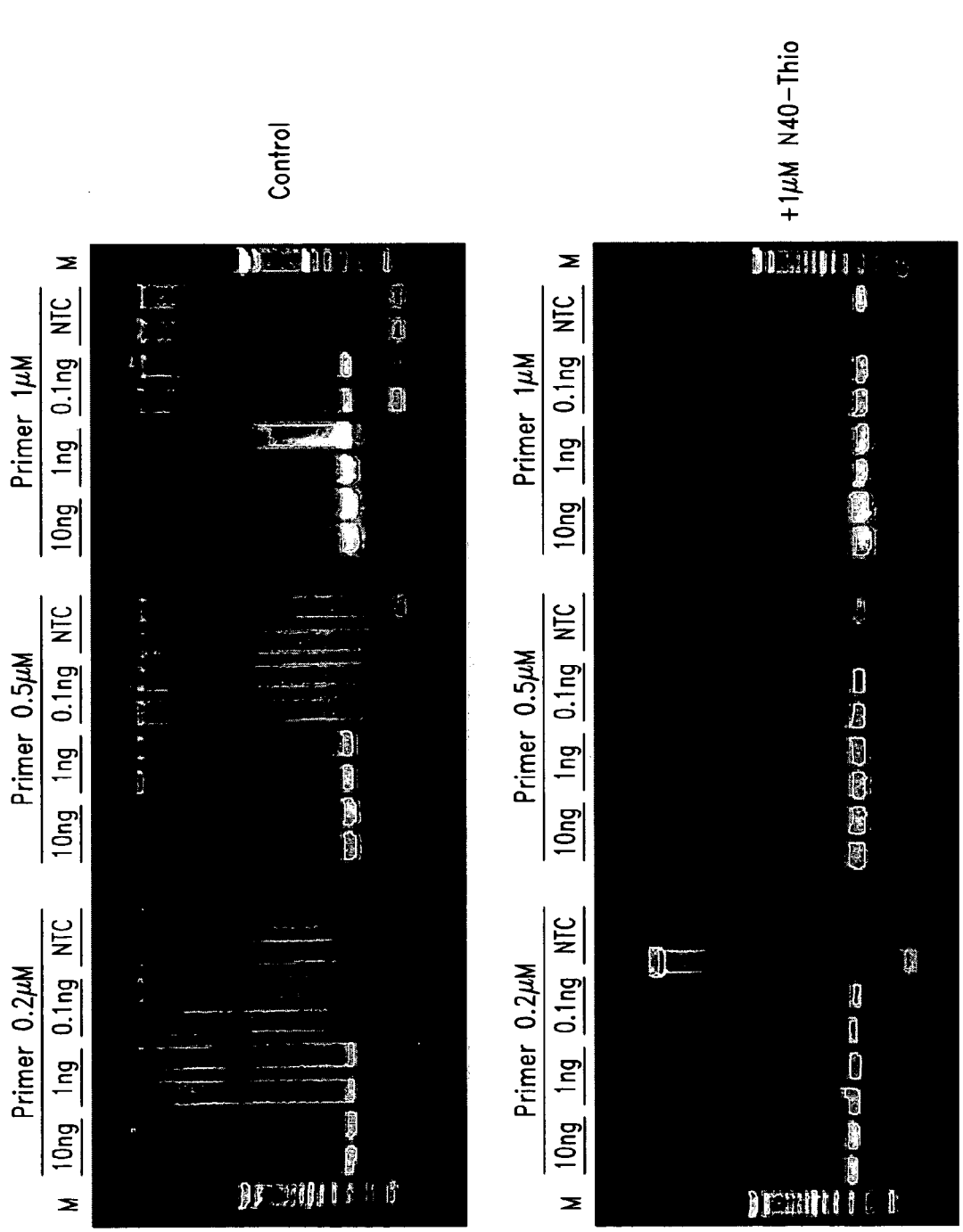
FIG. 13 an agarose gel analysis to investigate the effects of "feed" oligonucleotide N40-thio in conjunction with variable concentrations of the PCR primer on the amplification of β-actin.

NN*N [Phosp-Q]
(N: A, C, G, T; [Phosp-Q]: 3'-phosphate;
*: phosphothioate in the backbone 10 µl of each PCR reaction was analysed on an ethidium bromide stained agarose gel (2%). A 100 bp ladder (Invitrogen, 15628-050) served as a size standard. FIG. 13 shows the effect of "feed" oligonucleotide N40-thio in conjunction with blocked PCR primers on the amplification of β-Actin. M=marker.

Even with variable primer concentrations an improvement in yield and sensitivity was achieved in the presence of a "feed" oligonucleotide. At the same time, the background often appearing as "smear" in the high fidelity PCR reactions was clearly reduced.

General Methods

I. Template Nucleic Acid:
1. Genomic DNA: The human genomic DNA used (HuDNA and gDNA) was isolated from blood with a QIAamp DNA Blood Maxi Kit (QIAGEN, catalogue number 51192) or a FlexiGene DNA Kit (Qiagen, catalogue number 51204). The murine genomic DNA was extracted from NIH-3T3 cells with a DNeasy Tissue Kit (Qiagen, catalogue number 69504). The concentration of the isolated DNA was subsequently determined photometrically (OD260).
2. CDNA: Stands for "complementary DNA" and is the name for the single or double stranded DNA copies of a RNA molecule.

II. Production by Means of Reverse Transcription
1. RNA: Whole RNA from K562 cells was isolated with a RNeasy Midi Kit (QIAGEN, catalogue number 75142)
2. Reverse transcription: To produce cDNA, 1 µg of whole RNA was reverse transcribed with a Omniscript RT Kit (QUIAGEN, catalogue number 205110) using a mixture of random and oligo-dT(15) primers (random octamer 10 µM, oligonucleotide dT(15) 1 µM) according to the specifications in the handbook provided.

The invention claimed is:

1. A method for nucleic acid amplification, comprising amplifying a nucleic acid via performing a polymerase chain reaction (PCR) in the presence of (i) a DNA template, (ii) a DNA polymerase with proofreading activity, (iii) at least one primer, (iv) deoxyribonucleoside triphosphates, and (v) at least one target substrate,
   wherein the at least one primer is not resistant to degradation by the proofreading activity of the DNA polymerase,
   wherein the at least one target substrate
   (a) is a single stranded oligonucleotide in which at least one phosphate in the backbone of said single stranded oligonucleotide is replaced by at least one phosphorothioate,
   (b) is modified at its 3'-end so that it is incapable of being elongated by the DNA polymerase with proofreading activity,
   (c) has a random sequence,
   (d) forms a double stranded nucleic acid molecule with a strand of the DNA template under PCR conditions, and
   (e) is able as the double stranded nucleic acid molecule of (d) to serve as a binding site for the polymerase with proofreading activity, thereby reducing the 3'-exonuclease activity of the DNA polymerase toward the primer or the DNA template, and
   wherein the molecular ratio of the polymerase with proofreading activity to the at least one target substrate is between 1:1 and 1:1000.

2. The method according to claim 1, wherein the OH group at the 3'-end of the single stranded oligonucleotide is replaced with a phosphate group or another residue, or the single stranded oligonucleotide comprises a dideoxynucleotide, one or several inverse bases, RNA, an abasic site, a spacer, a dye, a quencher residue, or a modified base at its 3'-end.

3. The method according to claim 1, wherein the single stranded oligonucleotide has a length of 10 to 100 bases.

4. The method according to claim 1, wherein the single stranded oligonucleotide is present in the polymerase chain reaction in a concentration of 0.1 to 20 µM.

5. The method of claim 1, wherein the at least one target substrate forms a double stranded nucleic acid molecule with a strand of the DNA template during the annealing stage of the polymerase chain reaction.

6. The method of claim 5, wherein the annealing is carried out at a temperature between 40 and 70° C.

7. The method of claim 1, wherein at least the phosphate in the backbone of the single stranded oligonucleotide on the 3'-end between the last and penultimate bases is replaced by a phosphorothioate.

8. The method of claim 1, wherein the at least one target substrate is the oligonucleotide as set forth in SEQ ID NO: 22 in which the phosphate in the backbone on the 3'-end between the last and penultimate bases is replaced by a phosphorothioate, and the 3'-OH group is replaced with a 3'-phosphate group.

9. The method of claim 1, wherein the single stranded oligonucleotide has a length of 12 to 80 bases.

10. The method of claim 1, wherein the single stranded oligonucleotide has a length of 20 to 45 bases.

11. The method of claim 1, wherein the molecular ratio of the polymerase with proofreading activity to the single stranded oligonucleotide is between 1:1 and 1:500.

12. The method of claim 1, wherein the molecular ratio of the polymerase with proofreading activity to the single stranded oligonucleotide is between 1:1 and 1:200.

* * * * *

SEQUENCE LISTING

```
<160> NUMBER OF SEQ ID NOS: 22

<210> SEQ ID NO 1
<211> LENGTH: 22
<212> TYPE: DNA
<213> ORGANISM: Artificial Sequence
<220> FEATURE:
<223> OTHER INFORMATION: PCR primer sequence ERCC-1 (forward)

<400> SEQUENCE: 1
gctgtttgat gtcctgcacg ag                                          22

<210> SEQ ID NO 2
<211> LENGTH: 21
<212> TYPE: DNA
<213> ORGANISM: Artificial Sequence
<220> FEATURE:
<223> OTHER INFORMATION: PCR primer sequence ERCC-1 (reverse)

<400> SEQUENCE: 2
gcctggcctg ggaggacgat t                                           21
```

```
<210> SEQ ID NO 3
<211> LENGTH: 20
<212> TYPE: DNA
<213> ORGANISM: Artificial Sequence
<220> FEATURE:
<223> OTHER INFORMATION: Sequence of the "feed" oligonucleotide
      (P20-GAPDH)
<220> FEATURE:
<221> NAME/KEY: modified_base
<222> LOCATION: 20
<223> OTHER INFORMATION: 3 prime-phosphate

<400> SEQUENCE: 3
gcgtcaaagg tggaggagtg                                            20

<210> SEQ ID NO 4
<211> LENGTH: 30
<212> TYPE: DNA
<213> ORGANISM: Artificial Sequence
<220> FEATURE:
<223> OTHER INFORMATION: Sequence of the "feed" oligonucleotide
      (P30-GAPDH)
<220> FEATURE:
<221> NAME/KEY: modified_base
<222> LOCATION: 30
<223> OTHER INFORMATION: 3 prime -phosphate

<400> SEQUENCE: 4
gcgtcaaagg tggaggagtg ggtgtcgctg                                 30

<210> SEQ ID NO 5
<211> LENGTH: 45
<212> TYPE: DNA
<213> ORGANISM: Artificial Sequence
<220> FEATURE:
<223> OTHER INFORMATION: Sequence of the "feed" oligonucleotide
      (P45-GAPDH)
<220> FEATURE:
<221> NAME/KEY: modified_base
<222> LOCATION: 45
<223> OTHER INFORMATION: 3 prime -phosphate

<400> SEQUENCE: 5
gcgtcaaagg tggaggagtg ggtgtcgctg ttgaagtcag aggag                45

<210> SEQ ID NO 6
<211> LENGTH: 22
<212> TYPE: DNA
<213> ORGANISM: Artificial Sequence
<220> FEATURE:
<223> OTHER INFORMATION: PCR Primer sequence (CYST 3)

<400> SEQUENCE: 6
cccaaaccca acccatacac ac                                         22

<210> SEQ ID NO 7
<211> LENGTH: 22
<212> TYPE: DNA
<213> ORGANISM: Artificial Sequence
<220> FEATURE:
<223> OTHER INFORMATION: PCR Primer sequence (CYST 5)

<400> SEQUENCE: 7
ccttgcctta gatgtgtcgg ca                                         22

<210> SEQ ID NO 8
<211> LENGTH: 78
```

```
<212> TYPE: DNA
<213> ORGANISM: Artificial Sequence
<220> FEATURE:
<223> OTHER INFORMATION: Sequences of the "feed" oligonucleotides (P78
      3P)
<220> FEATURE:
<221> NAME/KEY: modified_base
<222> LOCATION: 78
<223> OTHER INFORMATION: 3 prime -phosphate

<400> SEQUENCE: 8
gcgtcaaagg tggaggagtg ggtgtcgctg ttgaagtcat gacttcaaca gcgacaccca    60
ctcctccacc tttgacgc                                                  78

<210> SEQ ID NO 9
<211> LENGTH: 78
<212> TYPE: DNA
<213> ORGANISM: Artificial Sequence
<220> FEATURE:
<223> OTHER INFORMATION: Sequences of the "feed" oligonucleotides (P78
      3P-thio)
<220> FEATURE:
<221> NAME/KEY: modified_base
<222> LOCATION: 77
<223> OTHER INFORMATION: phosphothioate in the backbone
<220> FEATURE:
<221> NAME/KEY: modified_base
<222> LOCATION: 78
<223> OTHER INFORMATION: 3 prime-phosphate

<400> SEQUENCE: 9
gcgtcaaagg tggaggagtg ggtgtcgctg ttgaagtcat gacttcaaca gcgacaccca    60
ctcctccacc tttgacgc                                                  78

<210> SEQ ID NO 10
<211> LENGTH: 26
<212> TYPE: DNA
<213> ORGANISM: Artificial Sequence
<220> FEATURE:
<223> OTHER INFORMATION: Sequences of the "feed" oligonucleotides
      (N14-degAATAAA)
<220> FEATURE:
<221> NAME/KEY: misc_feature
<222> LOCATION: 1, 2, 3, 4, 5, 6, 7, 8, 9, 10, 11, 12, 13, 14, 17
<223> OTHER INFORMATION: n = A,T,C or G

<400> SEQUENCE: 10
nnnnnnnnnn nnnnhhnddv aataaa                                         26

<210> SEQ ID NO 11
<211> LENGTH: 27
<212> TYPE: DNA
<213> ORGANISM: Artificial Sequence
<220> FEATURE:
<223> OTHER INFORMATION: Sequences of the "feed" oligonucleotides (pA-I)
<220> FEATURE:
<221> NAME/KEY: modified_base
<222> LOCATION: 1, 2, 3, 4, 5, 6, 7, 8, 9, 10, 11, 12, 13, 14, 15, 16,
      17, 18, 19, 20, 21
<223> OTHER INFORMATION: I

<400> SEQUENCE: 11
nnnnnnnnnn nnnnnnnnnn naataaa                                        27

<210> SEQ ID NO 12
<211> LENGTH: 35
<212> TYPE: DNA
<213> ORGANISM: Artificial Sequence
<220> FEATURE:
```

```
<223> OTHER INFORMATION: Sequences of the "feed" oligonucleotides
      (betaActp-6I-3)
<220> FEATURE:
<221> NAME/KEY: modified_base
<222> LOCATION: 30, 31, 32, 33, 34, 35
<223> OTHER INFORMATION: I

<400> SEQUENCE: 12
gtacactgac ttgagaccag ttgaataaan nnnnn                               35

<210> SEQ ID NO 13
<211> LENGTH: 25
<212> TYPE: DNA
<213> ORGANISM: Artificial Sequence
<220> FEATURE:
<223> OTHER INFORMATION: PCR Primer sequence (BACT-TM.5)

<400> SEQUENCE: 13
tcacccacac tgtgcccatc tacga                                          25

<210> SEQ ID NO 14
<211> LENGTH: 25
<212> TYPE: DNA
<213> ORGANISM: Artificial Sequence
<220> FEATURE:
<223> OTHER INFORMATION: PCR Primer sequence (BACT-TM.3)

<400> SEQUENCE: 14
cagcggaacc gctcattgcc aatgg                                          25

<210> SEQ ID NO 15
<211> LENGTH: 45
<212> TYPE: DNA
<213> ORGANISM: Artificial Sequence
<220> FEATURE:
<223> OTHER INFORMATION: Sequence of the "feed" oligonucleotide
      (GAP45-thio)
<220> FEATURE:
<221> NAME/KEY: modified_base
<222> LOCATION: 44
<223> OTHER INFORMATION: phosphothioate in the backbone
<220> FEATURE:
<221> NAME/KEY: modified_base
<222> LOCATION: 45
<223> OTHER INFORMATION: 3 prime -phosphate

<400> SEQUENCE: 15
gcgtcaaagg tggaggagtg ggtgtcgctg ttgaagtcag aggag                    45

<210> SEQ ID NO 16
<211> LENGTH: 45
<212> TYPE: DNA
<213> ORGANISM: Artificial Sequence
<220> FEATURE:
<223> OTHER INFORMATION: Sequence of the "feed" oligonucleotide
      (G45-TP-1sp-d)
<220> FEATURE:
<221> NAME/KEY: modified_base
<222> LOCATION: 23
<223> OTHER INFORMATION: abasic spacers
<220> FEATURE:
<221> NAME/KEY: modified_base
<222> LOCATION: 44
<223> OTHER INFORMATION: phosphothioate in the backbone
<220> FEATURE:
<221> NAME/KEY: modified_base
<222> LOCATION: 45
<223> OTHER INFORMATION: 3 prime -Phosphate

<400> SEQUENCE: 16
```

```
gcgtcaaagg tggaggagtg ggtgtcgctg ttgaagtcag aggag          45
```

<210> SEQ ID NO 17
<211> LENGTH: 45
<212> TYPE: DNA
<213> ORGANISM: Artificial Sequence
<220> FEATURE:
<223> OTHER INFORMATION: Sequence of the "feed" oligonucleotide
      (G45-TP-2sp-d)
<220> FEATURE:
<221> NAME/KEY: modified_base
<222> LOCATION: 11, 23
<223> OTHER INFORMATION: abasic spacers
<220> FEATURE:
<221> NAME/KEY: modified_base
<222> LOCATION: 44
<223> OTHER INFORMATION: phosphothioate in the backbone
<220> FEATURE:
<221> NAME/KEY: modified_base
<222> LOCATION: 45
<223> OTHER INFORMATION: 3 prime -Phosphate

<400> SEQUENCE: 17

```
gcgtcaaagg tggaggagtg ggtgtcgctg ttgaagtcag aggag          45
```

<210> SEQ ID NO 18
<211> LENGTH: 25
<212> TYPE: DNA
<213> ORGANISM: Artificial Sequence
<220> FEATURE:
<223> OTHER INFORMATION: PCR primer (beta-actin forward)
<220> FEATURE:
<221> NAME/KEY: modified_base
<222> LOCATION: 24
<223> OTHER INFORMATION: phosphothioate in the backbone

<400> SEQUENCE: 18

```
tcacccacac tgtgcccatc tacga                                25
```

<210> SEQ ID NO 19
<211> LENGTH: 25
<212> TYPE: DNA
<213> ORGANISM: Artificial Sequence
<220> FEATURE:
<223> OTHER INFORMATION: PCR primer (beta-actin reverse)
<220> FEATURE:
<221> NAME/KEY: modified_base
<222> LOCATION: 24
<223> OTHER INFORMATION: phosphothioate in the backbone

<400> SEQUENCE: 19

```
cagcggaacc gctcattgcc aatgg                                25
```

<210> SEQ ID NO 20
<211> LENGTH: 23
<212> TYPE: DNA
<213> ORGANISM: Artificial Sequence
<220> FEATURE:
<223> OTHER INFORMATION: PCR primer (MPUC 3)

<400> SEQUENCE: 20

```
gctgcttgaa gaaacgagcg gtg                                  23
```

<210> SEQ ID NO 21
<211> LENGTH: 24
<212> TYPE: DNA
<213> ORGANISM: Artificial Sequence
<220> FEATURE:
<223> OTHER INFORMATION: PCR primer (MPUC5 +258)

-continued

```
<400> SEQUENCE: 21
ctgcaccttc tggaattccg actc                                              24

<210> SEQ ID NO 22
<211> LENGTH: 39
<212> TYPE: DNA
<213> ORGANISM: Artificial Sequence
<220> FEATURE:
<223> OTHER INFORMATION: Sequence of the "feed" oligonucleotides
<220> FEATURE:
<221> NAME/KEY: modified_base
<222> LOCATION: 38
<223> OTHER INFORMATION: phosphothioate in the backbone
<220> FEATURE:
<221> NAME/KEY: modified_base
<222> LOCATION: 39
<223> OTHER INFORMATION: 3 prime - phosphate
<220> FEATURE:
<221> NAME/KEY: misc_feature
<222> LOCATION: 1, 2, 3, 4, 5, 6, 7, 8, 9, 10, 11, 12, 13, 14, 15, 16,
       17, 18, 19, 20, 21, 22, 23, 24, 25, 26, 27, 28, 29, 30, 31,
       32, 33, 34, 35, 36, 37, 38, 39
<223> OTHER INFORMATION: n = A,T,C or G

<400> SEQUENCE: 22
nnnnnnnnnn nnnnnnnnnn nnnnnnnnnn nnnnnnnnn                              39
```